United States Patent
Reisner et al.

(10) Patent No.: US 10,933,124 B2
(45) Date of Patent: *Mar. 2, 2021

(54) METHODS OF TRANSPLANTATION AND DISEASE TREATMENT

(71) Applicant: Yeda Research and Development Co. Ltd., Rehovot (IL)

(72) Inventors: Yair Reisner, Old Jaffa (IL); Noga Or-Geva, Rehovot (IL); Eran Ophir, Rehovot (IL); Yaki Eidelstein, Rehovot (IL); Rotem Gidron Budovsky, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/744,881

(22) PCT Filed: Jul. 14, 2016

(86) PCT No.: PCT/IL2016/050774
§ 371 (c)(1),
(2) Date: Jan. 15, 2018

(87) PCT Pub. No.: WO2017/009852
PCT Pub. Date: Jan. 19, 2017

(65) Prior Publication Data
US 2018/0207247 A1    Jul. 26, 2018

Related U.S. Application Data

(60) Provisional application No. 62/193,207, filed on Jul. 16, 2015, provisional application No. 62/193,229, filed on Jul. 16, 2015.

(51) Int. Cl.
| | |
|---|---|
| *A61K 35/17* | (2015.01) |
| *A61P 31/00* | (2006.01) |
| *A61P 35/04* | (2006.01) |
| *A61K 39/00* | (2006.01) |
| *C12N 5/078* | (2010.01) |
| *C12N 5/0783* | (2010.01) |
| *A61K 39/395* | (2006.01) |
| *C07K 16/28* | (2006.01) |
| *A61K 35/12* | (2015.01) |

(52) U.S. Cl.
CPC ............ *A61K 39/001* (2013.01); *A61K 35/17* (2013.01); *A61K 39/39566* (2013.01); *A61P 31/00* (2018.01); *A61P 35/04* (2018.01); *C07K 16/2896* (2013.01); *C12N 5/0636* (2013.01); *C12N 5/0637* (2013.01); *C12N 5/0648* (2013.01); *A61K 2035/122* (2013.01); *A61K 2039/5158* (2013.01); *C12N 2501/2307* (2013.01); *C12N 2501/2315* (2013.01); *C12N 2501/2321* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,447,765 B1 | 9/2002 | Horwitz | |
| 6,759,035 B2 | 7/2004 | Horwitz | |
| 6,803,036 B1 | 10/2004 | Horwitz | |
| 7,270,810 B2 | 9/2007 | Reisner et al. | |
| 8,974,779 B2* | 3/2015 | Reisner | A61K 35/28 424/93.7 |
| 9,421,228 B2* | 8/2016 | Reisner | A61K 39/001 |
| 9,738,872 B2* | 8/2017 | Reisner | A61K 39/001 |
| 9,833,482 B2* | 12/2017 | Reisner | A61K 35/42 |
| 9,987,354 B2* | 6/2018 | Fraser | A61K 39/00 |
| 9,993,548 B2* | 6/2018 | Maldonado | A61K 39/00 |
| 10,039,822 B2* | 8/2018 | Altreuter | A61K 39/00 |
| 10,155,818 B2* | 12/2018 | Seibert | C07K 16/2878 |
| 10,280,226 B2* | 5/2019 | Seibert | C07K 16/2878 |
| 10,369,172 B2* | 8/2019 | Reisner | |
| 2002/0182211 A1 | 12/2002 | Peach et al. | |
| 2003/0003083 A1 | 1/2003 | Reisner et al. | |
| 2003/0022836 A1 | 1/2003 | Larsen et al. | |
| 2003/0049235 A1 | 3/2003 | Reisner | |
| 2003/0083246 A1 | 5/2003 | Cohen et al. | |
| 2004/0022787 A1 | 2/2004 | Cohen et al. | |

(Continued)

FOREIGN PATENT DOCUMENTS

| | | |
|---|---|---|
| EP | 2753351 | 3/2013 |
| JP | 2008-521406 | 6/2008 |

(Continued)

OTHER PUBLICATIONS

Or-Geva et al, Leukemia, 2017, 32:1038-1040 (Year: 2017).*
Lask et al, Blood, Apr. 11, 2013, 121/15:3033-3040. prepublished online: Feb. 27, 2013 (Year: 2013).*
Ophir et al, Best Practice & Research CLinical Haematology, 2011, 24:393-401 (Year: 2011).*
Ophir et al, Blood, Feb. 14, 2013, 121/7:1220-1228. prepublished online: Dec. 5, 2012 (Year: 2013).*

(Continued)

*Primary Examiner* — Nita M. Minnifield

(57) ABSTRACT

A method of transplantation is disclosed. The method comprising administering to a subject in need of transplantation of cells in suspension, a therapeutically effective amount of anti-third party cells having a central memory T-lymphocyte (Tcm) phenotype, said anti-third party cells being tolerance-inducing cells and capable of homing to the lymph nodes following transplantation, wherein said cells in suspension comprise non-hematopoietic cells or hematopoietic cells which are not stem cells. Methods of treating and kits are also provided.

31 Claims, 10 Drawing Sheets

(5 of 10 Drawing Sheet(s) Filed in Color)

(56) References Cited

U.S. PATENT DOCUMENTS

| | | | |
|---|---|---|---|
| 2004/0136972 A1* | 7/2004 | Reisner | A61K 39/001 424/93.7 |
| 2005/0123539 A1 | 6/2005 | Rusnak | |
| 2005/0214313 A1 | 9/2005 | Peach et al. | |
| 2006/0269973 A1 | 11/2006 | Yee | |
| 2007/0009511 A1 | 1/2007 | Hagerty et al. | |
| 2007/0264274 A1 | 11/2007 | Reisner et al. | |
| 2008/0131415 A1 | 6/2008 | Riddell et al. | |
| 2008/0160022 A1 | 7/2008 | Larsen et al. | |
| 2008/0279817 A1 | 11/2008 | Skak | |
| 2009/0022730 A1 | 1/2009 | Raulf et al. | |
| 2009/0041769 A1 | 2/2009 | Peach et al. | |
| 2009/0041790 A1 | 2/2009 | Rusnak | |
| 2009/0068203 A1 | 3/2009 | Rusnak | |
| 2009/0232774 A1 | 9/2009 | Reisner | |
| 2010/0022627 A1 | 1/2010 | Scherer | |
| 2010/0041602 A1 | 2/2010 | Hagerty et al. | |
| 2010/0049935 A1 | 2/2010 | Pichumani et al. | |
| 2010/0166756 A1 | 7/2010 | Cohen et al. | |
| 2010/0183612 A1 | 7/2010 | Peach et al. | |
| 2010/0255009 A1* | 10/2010 | Siemionow | A61K 31/436 424/173.1 |
| 2011/0212071 A1 | 9/2011 | Reisner et al. | |
| 2013/0171108 A1* | 7/2013 | Reisner | A61K 39/001 424/93.3 |
| 2013/0183322 A1 | 7/2013 | Reisner et al. | |
| 2014/0120622 A1 | 5/2014 | Gregory et al. | |
| 2014/0212398 A1* | 7/2014 | Reisner | A61K 39/001 424/93.71 |
| 2014/0314795 A1 | 10/2014 | Riddell et al. | |
| 2016/0354410 A1* | 12/2016 | Reisner | A61K 39/001 |
| 2018/0193384 A1* | 7/2018 | Reisner | A61K 39/001 |
| 2018/0200300 A1* | 7/2018 | Reisner | A61K 35/17 |
| 2018/0207247 A1* | 7/2018 | Reisner | A61K 35/17 |
| 2018/0207272 A1* | 7/2018 | Reisner | A61K 35/17 |
| 2019/0091266 A1* | 3/2019 | Reisner | A61P 11/00 |
| 2019/0338247 A1 | 11/2019 | Reisner et al. | |

FOREIGN PATENT DOCUMENTS

| | | | |
|---|---|---|---|
| JP | 2013-537187 | 9/2013 | |
| JP | 2014-526244 | 7/2014 | |
| JP | 2014-510108 | 10/2014 | |
| WO | WO 01/49243 | 7/2001 | |
| WO | WO 02/43651 | 6/2002 | |
| WO | WO 02/102971 | 12/2002 | |
| WO | WO 2005/067956 | 7/2005 | |
| WO | WO 2005/092380 | 10/2005 | |
| WO | WO 2006/041763 | 4/2006 | |
| WO | WO 2006/065495 | 6/2006 | |
| WO | WO 2007/023491 | 3/2007 | |
| WO | WO 2009/053109 | 4/2009 | |
| WO | WO 2010/049935 | 5/2010 | |
| WO | WO 2011/053223 | 5/2011 | |
| WO | WO 2011/140170 | 11/2011 | |
| WO | WO 2012/032525 | 3/2012 | |
| WO | WO 2012/032526 | 3/2012 | |
| WO | WO 2012/129514 | 9/2012 | |
| WO | WO 2013/035099 | 3/2013 | |
| WO | WO-2013035099 A1 * | 3/2013 | A61K 39/001 |
| WO | WO 2014/031687 | 2/2014 | |
| WO | WO 2014/039044 | 3/2014 | |
| WO | WO 2014/059173 | 4/2014 | |
| WO | WO 2014/152177 | 9/2014 | |
| WO | WO 2017/009852 | 1/2017 | |
| WO | WO 2017/009853 | 1/2017 | |
| WO | WO-2017009853 A1 * | 1/2017 | A61K 35/17 |
| WO | WO-2017203520 A1 * | 11/2017 | A61P 11/00 |
| WO | WO 2018/134824 | 7/2018 | |
| WO | WO-2018134824 A1 * | 7/2018 | A61K 35/17 |

OTHER PUBLICATIONS

Requisition by the Examiner Dated Jul. 30, 2018 From the Innovation, Science and Economic Development Canada, Canadian Intellectual Property Office Re. Application No. 2,848,121. (5 Pages).

Notification of Office Action and Search Report dated Feb. 26, 2019 From the National Intellectual Property Administration of the People's Republic of China Re. Application No. 201610307275.9 and Its Translation Into English. (20 Pages).

Applicant-Initiated Interview Summary dated May 4, 2015 From the US Patent and Trademark Office Re. U.S. Appl. No. 13/821,255.

Communication Pursuant to Article 94(3) EPC dated Jun. 4, 2014 From the European Patent Office Re. Application No. 09764302.7.

Communication Pursuant to Article 94(3) EPC dated Dec. 14, 2012 From the European Patent Office Re. Application No. 09764302.7.

Communication Pursuant to Article 94(3) EPC dated Oct. 21, 2015 From the European Patent Office Re. Application No. 12769743.1.

Communication Pursuant to Article 94(3) EPC dated Jan. 24, 2014 From the European Patent Office Re. Application No. 11773345.6.

Communication Pursuant to Article 94(3) EPC dated Jan. 26, 2015 From the European Patent Office Re. Application No. 12769743.1.

Communication Pursuant to Article 94(3) EPC dated Jan. 27, 2014 From the European Patent Office Re. Application No. 11773325.3.

Decision on Rejection dated Dec. 2, 2015 From The State Intellectual Property Office of the People's Republic of China Re. Application No. 201180053858.9 and Its Translation Into English.

Examination Report dated Feb. 1, 2017 From the Instituto Mexicano de la Propiedad Industrial, IMPI, Direccion Divisional de Patentes Re. Application No. MX/a/2013/002668 and Its Translation Into English. (8 Pages).

Examination Report dated Feb. 2, 2016 From the Intellectual Property Office of Singapore Re. Application No. 11201400513P.

Examination Report dated Oct. 15, 2015 From the Intellectual Property Office of Singapore Issued by the Austrian Patent Office Re. Application No. 201301743-9.

Examination Report dated Sep. 25, 2017 From the Instituto Mexicano de la Propiedad Industrial, IMPI, Direccion Divisional de Patentes Re. Application No. MX/a/2013/002668 and Its Translation Into English. (16 Pages).

Examination Report dated Jul. 28, 2017 From the Australian Government, IP Australia Re. Application No. 2012305931. (3 Pages).

Examination Report dated Mar. 28, 2016 From the Government of India, Patent Office, Intellectual Property Building Re. Application No. 905/MUMNP/2011.

Examination Report dated Jul. 29, 2016 From the Instituto Mexicano de la Propiedad Industrial, IMPI, Direccion Divisional de Patentes Re. Application No. MX/a/2013/002668 and Its Translation Into English.

International Preliminary Report on Patentability dated May 12, 2011 From the International Bureau of WIPO Re. Application No. PCT/IL2009/001014.

International Preliminary Report on Patentability dated Mar. 20, 2014 From the International Bureau of WIPO Re. Application No. PCT/IL2012/050354.

International Preliminary Report on Patentability dated Mar. 21, 2013 From the International Bureau of WIPO Re. Application No. PCT/IL2011/000726.

International Preliminary Report on Patentability dated Mar. 21, 2013 From the International Bureau of WIPO Re. Application No. PCT/IL2011/000727.

International Preliminary Report on Patentability dated Jan. 25, 2018 From the International Bureau of WIPO Re. Application No. PCT/IL2016/050774. (7 Pages).

International Preliminary Report on Patentability dated Jan. 25, 2018 From the International Bureau of WIPO Re. Application No. PCT/IL2016/050775. (7 Pages).

International Search Report and the Written Opinion dated Mar. 7, 2012 From the International Searching Authority Re. Application No. PCT/IL2011/000727.

International Search Report and the Written Opinion dated Feb. 16, 2010 From the International Searching Authority Re. Application No. PCT/IL2009/001014.

International Search Report and the Written Opinion dated Oct. 19, 2016 From the International Searching Authority Re. Application No. PCT/IL2016/050774.

(56) References Cited

OTHER PUBLICATIONS

International Search Report and the Written Opinion dated Oct. 19, 2016 From the International Searching Authority Re. Application No. PCT/IL2016/050775.
International Search Report and the Written Opinion dated Jun. 27, 2012 From the International Searching Authority Re. Application No. PCT/IL2011/000726.
International Search Report and the Written Opinion dated Jan. 28, 2013 From the International Searching Authority Re. Application No. PCT/IL2012/050354.
Notice of Allowance dated Apr. 11, 2017 From the US Patent and Trademark Office Re. U.S. Appl. No. 13/126,472. (34 pages).
Notice of Reason for Rejection dated Jul. 1, 2016 From the Japanese Patent Office Re. Application No. 2014-529143 and Its Translation Into English.
Notice of Reason for Rejection dated Aug. 4, 2015 From the Japanese Patent Office Re. Application No. 2013-527738 and Its Translation Into English.
Notification of Lack of Unity dated Feb. 21, 2017 From the Federal Service for Intellectual Property, Rospatent, Federal State Budgetary Institution, Federal Institute of industrial Property, Patents and Trademarks of the Russion Federation Re. Application No. 2014110897 and Its Translation Into English. (8 Pages).
Notification of Office Action and Search Report dated Jan. 23, 2015 From the State Intellectual Property Office of the People's Republic of China Re. Application No. 201280054739.X.
Office Action dated Nov. 3, 2016 From the Israel Patent Office Re. Application No. 231397 and Its Translation Into English. (7 Pages).
Office Action dated Oct. 12, 2015 From the Israel Patent Office Re. Application No. 225102 and Its Translation Into English.
Office Action dated May 14, 2014 From the Israel Patent Office Re. Application No. 212587 and Its Translation Into English.
Office Action dated Apr. 15, 2013 From the Israel Patent Office Re. Application No. 212587 and Its Translation Into English.
Office Action dated Mar. 18, 2015 From The State Intellectual Property Office of the People's Republic of China Re. Application No. 201180053858.9 and Its Translation Into English.
Office Action dated Sep. 23, 2015 From the State Intellectual Property Office of the People's Republic of China Re. Application No. 201280054739.X and Its Translation Into English.
Office Action dated Apr. 29, 2014 From The State Intellectual Property Office of the People's Republic of China Re. Application No. 201180053858.9 and Its Translation Into English.
Official Action dated Aug. 1, 2013 From the US Patent and Trademark Office Re. U.S. Appl. No. 13/126,472.
Official Action dated Jun. 1, 2017 From the US Patent and Trademark Office Re. U.S. Appl. No. 14/343,053. (27 pages).
Official Action dated Oct. 3, 2016 From the US Patent and Trademark Office Re. U.S. Appl. No. 13/126,472.
Official Action dated Oct. 7, 2016 From the US Patent and Trademark Office Re. U.S. Appl. No. 14/343,053.
Official Action dated May 8, 2014 From the US Patent and Trademark Office Re. U.S. Appl. No. 13/126,472.
Official Action dated Feb. 12, 2016 From the US Patent and Trademark Office Re. U.S. Appl. No. 14/343,053.
Official Action dated Nov. 19, 2015 From the US Patent and Trademark Office Re. U.S. Appl. No. 13/126,472.
Official Action dated Dec. 23, 2016 From the US Patent and Trademark Office Re. U.S. Appl. No. 14/343,053. (17 pages).
Official Action dated Mar. 23, 2015 From the US Patent and Trademark Office Re. U.S. Appl. No. 13/821,255.
Official Action dated Jul. 24, 2014 From the US Patent and Trademark Office Re. U.S. Appl. No. 13/821,255.
Patent Examination Report dated Aug. 23, 2016 From the Australian Government, IP Australia Re. Application No. 2012305931.
Restriction Official Action dated Aug. 14, 2014 From the US Patent and Trademark Office Re. U.S. Appl. No. 13/821,269.
Restriction Official Action dated Oct. 20, 2015 From the US Patent and Trademark Office Re. U.S. Appl. No. 14/343,053.
Restriction Official Action dated Dec. 22, 2017 From the US Patent and Trademark Office Re. U.S. Appl. No. 15/242,666. (8 pages).
Search Report and Written Opinion dated Oct. 10, 2014 From the Intellectual Property Office of Singapore Re. Application No. 11201400513P.
Search Report dated Apr. 29, 2014 From The State Intellectual Property Office of the People's Republic of China Re. Application No. 201180053858.9 and Its Translation Into English.
Translation dated Feb. 8, 2015 of Notification of Office Action and Search Report dated Jan. 23, 2015 From the State Intellectual Property Office of the People's Republic of China Re. Application No. 201280054739.X.
Translation of Office Action dated Dec. 27, 2012 From the State Intellectual Property Office of the People's Republic of China Re. Application No. 200980153053.4.
Translation of Search Report dated Dec. 27, 2012 From the State Intellectual Property Office of the People's Republic of China Re. Application No. 200980153053.4.
Written Opinion and Search Report dated Feb. 28, 2014 From the Intellectual Property Office of Singapore Issued by the Austrian Patent Office Re. Application No. 201301743-9.
Written Opinion dated Jun. 11, 2015 From the Intellectual Property Office of Singapore Re. Application No. 11201400513P.
Written Opinion dated Feb. 17, 2015 From the Intellectual Property Office of Singapore Issued by the Austrian Patent Office Re. Application No. 201301743-9.
Albrecht et al. "IL-21-Treated Naive CD45RA+ CD8+ T Cells Repressant A Reliable Source for Producing Leukemia-Reactive Cytotoxic T Lymphocytes With High Proliferative Potential and Early Differentiation Phenotype", Cancer Immunology, Immunotherapy: CII, XP002689103, 60(2): 235-248, Feb. 2011. Abstract.
Arditti et al. "Eradication of B-CLL by Autologous and Allogeneic Host Nonreactive Anti-Third-Party CTLs", Blood, 105(8): 3365-3371, Apr. 15, 2005.
Aversa et al. "Full Haplotype-Mismatched Hematopoietic Stem-Cell Transplantation: A Phase II Study in Patients With Acute Leukemia at High Risk of Relapse", Journal of Clinical Oncology, 23(15): 3447-3454, May 20, 2005.
Aversa et al. "Successful Engraftment of T-Cell-Depleted Haploidentical 'Three-Loci' Incompatible Transplants in Leukemia Patients by Addition of Recombinant Human Granulocyte Colony-Stimulating Factor-Mobilized Peripheral Blood Progenitor Cells to Bone Marrow Inoculum", Blood, 84(4): 3948-3955, Dec. 1, 1994.
Aversa et al. "Treatment of High-Risk Acute Leukemia With T-Cell-Depleted Stem Cells From Related Donors With One Fully Mismatched HLA Haplotype", The New England Journal of Medicine, 339(17): 1186-1193, Oct. 22, 1998.
Aviner et al. "Large-Scale Preparation of Human Anti-Third-Party Veto Cytotoxic T Lymphocytes Depleted of Graft-Versus-Host Reactivity: A New Source for Graft Facilitating Cells in Bone Marrow Transplantation", Human Immunology, 66(6): 644-652, Jun. 30, 2005.
Bachar-Lustig et al. "Anti-Third-Party Veto CTLs Overcome Rejection of Hematopoietic Allografts: Synergism With Rapamycin and BM Cell Dose", Blood, 102(6): 1943-1950, Sep. 15, 2003.
Bachar-Lustig et al. "Megadose of T Cell-Depleted Bone Marrow Overcomes MHC Barriers in Sublethally Irradiated Mice", Nature Medicine, 1(12): 1268-1273, Dec. 1995.
Berger et al. "Adoptive Transfer of Effector CD8+ T Cells Derived from Central Memory Cells Establishes Persistent T cell Memory in Primates", The Journal of Clinical Investigation, 118(1): 294-305, Jan. 2008.
Biocompare "Human CD8+ T Cell Isolation Kit II From Miltenyi Biotec", Biocompare, pp. 1-5, Oct. 30, 2006.
Dutton et al. "T Cell Memory", Annual Review of Immunology, 16: 201-223, 1998. p. 203, 2nd Para.
Fujiwara "Adoptive Immunotherapy for Hematological Malignancies Using T Cells Gene-Modified to Express Tumor Antigen-Specific Receptors", Pharmaceuticals, 7(12): 1049-1068, Dec. 15, 2014.
Gilham et al. "Adoptive T-Cell Therapy for Cancer in the United Kingdom: A Review of Activity for the British Society of Gene and

(56) References Cited

OTHER PUBLICATIONS

Cell Therapy Annual Meeting 2015", Human Gene Therapy, 26(5): 276-285, Published Online Apr. 10, 2015.
Gouble et al. "In Vivo Proof of Concept of Activity and Safety of UCART19, an Allogeneic 'Off-the-Shelf' Adoptive T-Cell Immunotherapy Against CD19+ B-Cell Leukemias", Blood, 124(21): 4689, Dec. 6, 2014.
Grigg et al. "Graft-Versus-Lymphoma Effects: Clinical Review, Policy Proposal, and Immunobiology", Biology of Blood and Marrow Transplantation, 10: 579-590, 2004.
Gur et al. "Immune Regulatory Activity of CD34+ Progenitor Cells: Evidence for a Deletion-Based Mechanism Mediated by TNF-{Alpha}", Blood, 105(6): 2585-2593, Mar. 15, 2005.
Gur et al. "Tolerance Induction by Megadose Hematopoietic Progenitor Cells: Expansion of Veto Cells by Short-Term Culture of Purified Human CD34+ Cells", Blood, 99(11): 4174-4181, Jun. 1, 2002.
Handgretinger et al. "Megadose Transplantation of Purified Peripheral Blood CD34+ Progenitor Cells From HLA-Mismatched Parental Donors in Children", Bone Marrow Transplantation, 27: 777-783, 2001.
Harwerth et al. "Monoclonal Antibodies Directed to the ErbB-2 Receptor Inhibit In Vivo Tumour Cell Growth", British Journal of Cancer, 68(6): 1140-1145, Dec. 1993.
Hecht et al. "Embryonic Pig Pancreatic Tissue for the Treatment of Diabetes in a Nonhuman Primate Model", Proc. Natl. Acad. Sci. USA, PNAS, XP009122169, 106(21): 8659-8664, May 26, 2009. p. 8663, col. 1, Para 2.
Ho et al. "Adoptive Therapy With CD8+ T Cells: It May Get by With a Little Help From Its Friends", the Journal of Clinical Investigation, 110(10): 1415-1417, Nov. 2002.
Huarte et al. "Ex Vivo Expansion of Tumor Specific Lymphocytes With IL-15 and IL-21 for Adoptive Immunotherapy in Melanoma", Cancer Letters, 285: 80-88, 2009. Abstract, p. 80, Left Right Col., 2nd Para, Section 2.4.
Kawai et al. "HLA-Mismatched Renal Transplantation Without Maintenance Immunosuppression", The New England Journal of Medicine, XP002562461, 358(4): 353-361, Jan. 24, 2008. Abstract, p. 353-354, col. 1, Para 2, Table 1.
Lapidot et al. "Enhancement by Dimethyl Myleran of Donor Type Chimerism in Murine Recipients of Bone Marrow Allografts", Blood, 73(7): 2025-2032, May 15, 1989.
Lapidot et al. "Enhancement by Dimethyl Myleran of Donor type Chimerism in Murine Resipients of Bone Marrow Allografts", Blood, 73(7): 2025-2032, May 15, 1989.
Lask et al. "TCR Independent Killing of B Cell Malignancies by Anti-3rd Party CTLs: Rapid Conjugate Formation Via ICAM1-LFA1 Leads to Slow Induction of Apoptosis Upon MHC-CD8 Engagement", Journal of Immunology, XP009156306, 187(4): 2006-2014, Aug. 15, 2011.
Li et al. "IL-21 Influences the Frequency, Phenotype, and Affinity of the Antigen-Specific CD8 T Cell Response", The Journal of Immunology, 175: 2261-2269, 2005. Abstract, Materials and Methods: Induction of Human Ag-Specific CD8+ T Cells.
Markley et al. "IL-7 and IL-21 Are Superior to IL-2 and IL-15 in Promoting Human T Cell-Mediated Rejection of Systematic Lymphoma in Immunodeficient Mice", Blood, XP009165652, 115(17): 3508-3519, Apr. 29, 2010. p. 3509, col. 2, Par 2.
Ophir et al. "Induction of Tolerance in Organ Recipients by Hematopoietic Stem Cell Transplantation", International Immunopharmacology, XP026088865, 9(6): 694-700, Jun. 1, 2009. Figs.3, 6.
Ophir et al. "Induction of Tolerance to Bone Marrow Allografts by Donor-Derived Host Nonreactive Ex Vivo Induced Central Memory CD8 T Cells", Blood, XP009165643, 115(10): 2095-2104, Mar. 11, 2010. Abstract, p. 2096, col. 1, Para 2.
Ophir et al. "Induction of Transplantation Tolerance in Haploidenical Transplantation Under Reduced Intensity Conditioning: The Role of Ex-Vivo Generated Donor CD8+ T Cells With Central Memory Phenotype", Best Practice & Research Clinical Haematology, XP002829486, 24(3): 393-401, Jul. 13, 2011. p. 396, Fig.3.
Pilat et al. "Treg-Therapy Allows Mixed Chimerism and Transplantation Tolerance Without Cytoreductive Conditioning", American Journal of Transplantation, 10: 751-762, 2010.
Rachamim et al. "Tolerance Induction by 'Megadose' Hematopoietic Transplants. Donor-Type CD34 Stem Cells Induce Potent Specific Reduction of Host anti-Donor Cytotoxic T Lymphocyte Precursors in Mixed Lymphocyte Culture", Transplantation, 65(10): 1386-1393, May 27, 1998.
Reich-Zeliger et al. "Anti-Third Party CD8+ CTLs as Potent Veto Cells: Coexpression of CD8 and FasL Is a Prerequisite", Immunity, 13: 507-515, Oct. 2000.
Reich-Zeliger et al. "Tolerance Induction by Veto CTLs in the TCR Transgenic 2C Mouse Model. I. Relative Reactivity of Different Veto Cells", The Journal of Immunology, 173(11): 6654-6659, Dec. 2004.
Reisner et al. "Bone Marrow Transplantation Across HLA Barriers by Increasing the Number of Transplanted Cells", Immunology Today, 16(9): 437-440, 1995.
Reisner et al. "Demonstration of Clonable Alloreactive Host T Cells in a Primate Model for Bone Marrow Transplantation", Proc. Natl. Acad. Sci. USA, 83: 4012-415, Jun. 1986.
Reisner et al. "Stem Cell Escalation Enables HLA-Disparate Haematopoietic Transplants in Leukaemia Patients", Immunology Today, 20(8): 343-347, Aug. 1999.
Roncarolo et al. "Regulatory T-Cell Immunotherapy for Tolerance to Self Antigens and Alloantigens in Humans", Nature Reviews Immunology, 7(8): 585-598, Aug. 2007.
Santegoets et al. "In Vitro Priming of Tumor-Specific Cytotoxic T Lymphocytes Using Allogeneic Dendritic Cells Derived From the Human MUTZ-3 Cell Line", Cancer Immunol Immunother, 55(12): 1480-1490, Published Online Feb. 9, 2006.
Scandling et al. "Tolerance and Chimerism After Renal and Hematopoietic-Cell Tranplantation", The New England Journal of Medicine, XP002562462, 358(4): 362-368, Jan. 24, 2008. Abstract, p. 363-365, Fig.3, Abstract, p. 362, Para 1, 3-p. 363, Left Col., Para 2, Right Col., Para 2, 4, p. 365, Left Col., Para 2, p. 367, Discussion, Figs.2, 3.
Sharpe et al. "Genetically Modified T Cells in Cancer Therapy: Opportunities and Challenges", Disease Models and Mechanisms, 8(4): 337-350, Apr. 2015.
Tchorsh-Yutsis et al. "Pig Embryonic Pancreatic Tissue as a Source for Transplantation in Diabetes. Transient Treatment With Anit-LFA1, Anit-CD48, and FTY720 Enables Long-Term Graft Maintenance in Mice With Only Mild Ongoing Immunosuppression", Diabetes, XP009122170, 58(7): 1585-1594, Jul. 1, 2009. Figs.5, 7, Table 1.
Uharek et al. "Influence of Cell Dose and Graft-Versus-Host Reactivity on Rejection Rates After Allogeneic Bone Marrow Transplantation", Blood, 79(6): 1612-1621, Mar. 15, 1992.
Weninger et al. "Migratory Properties of Naive, Effector, and Memory CD8+ T Cells", Journal of Experimental Medicine, 12(6): 953-966, Oct. 1, 2001.
Wherry et al. "Lineage Relationship and Protective Immunity of Memory CD8 T Cell Subsets", Nature Immunology, XP002562463, 4(3): 225-234, Mar. 2003. p. 232-233, Figs.1-4.
Woelfl et al. "Primed Tumor-Reactive Multifunctional CD62L+ Human CD8+ T Cells for Immunotherapy", Cancer Immunology, Immunotherapy, 60(2): 173-186, Feb. 2011.
Xie "The Development of the PBSC Transplantation", Railway Medical Journal, 29(5): 281-283, Jan. 31, 2001. & English Translation.
Yang et al. "In Vitro Generated Anti-Tumor T Lymphocytes Exhibit Distinct Subsets Mimicking In Vivo Antigen-Experienced Cells", Cancer Immunology, Immunotherapy: CII, XP009165653, 60(5): 739-749, May 2011.
Zeng et al. "Synergy of IL-21 and IL-15 in Regulating CD8+ T Cell Expansion and Function", The Journal of Experimental Medicine, 201(1): 139-148, Jan. 3, 2005.
International Search Report and the Written Opinion dated Apr. 17, 2018 From the International Searching Authority Re. Application No. PCT/IL2018/050071. (17 Pages).

(56) References Cited

OTHER PUBLICATIONS

Ersek et al. "Unique Patterns of CD8+ T-Cell-Mediated Organ Damage in the Act-mOVA/OT-I Model of Acute Graft-Versus-Host Disease", Cellular and Molecular Life Sciences, CMLS, XP036053921, 73(20): 3935-3947, Published Online Apr. 30, 2016.
Geva et al. "The Role of Donor-Derived Veto Cells in Nonmyeloablative Haploidentical HSCT", Bone Marrow Transplantation, XP055461528, 50(S2): S14-S20, Jun. 1, 2015. p. 16-17.
Rajawat et al. "Development of an Enhanced VETO Cells for the Generation of Alloantigen-Specific Tolerance", The Journal of Immunology, XP055462318, 196(1 Suppl.): 140.24, May 1, 2016. Abstract.
Rajawat et al. "Induction of Antigen Specific Transplantation Tolerance Using Chimeric Antigen Receptor Type T Cells Engineered to Kill Allospecific T Cells by a Gene Therapy Immunotherapeutic Approach (TRAN2P.968)", The Journal of Immunology, XP055462376, 194(1 Suppl.): 209.8, May 1, 2015. Abstract.
Official Action dated Jul. 17, 2019 From the US Patent and Trademark Office Re. U.S. Appl. No. 15/744,905. (43 pages).
Neeson et al. "Ex vivo culture of chimeric antigen receptor T cells generates functional CO8+ T cells with effector and central memory-like phenotype", Gene Therapy, 17: 1105-1116, 2010.
Official Action dated Jun. 19, 2018 From the US Patent and Trademark Office Re. U.S. Appl. No. 15/242,666. (54 pages).
Carrio et al. "Initial Antigen Encounter Programs CD8+ TCells Competent to Develop into Memory Cells That Are Activated in an Antigen-Free, IL-7- and IL-15-Rich Environment", The Journal of Immunology, 172: 7315-7323, 2004.
Doiron et al. "The Role of T Cells in Peripheral Blood Mononuclear Cells", Human Tissue Sample Blog, pp. 1-4, 2016.
Klinger et al. "Cyclical Expression of L-Selectin (CD62L) by Recirculating T Cells", International Immunology, 21(4): 443-455, Apr. 1, 2009.
Van Leeuwen et al. "Proliferation Requirements of Cytomegalovirus-Specific, Effector-Type Human CD8+ T Cells", The Journal of Immunology,169: 5838-5843, 2002.
Official Action dated May 21, 2019 From the US Patent and Trademark Office Re. U.S. Appl. No. 15/242,666. (34 pages).
International Preliminary Report on Patentability dated Aug. 1, 2019 From the International Bureau of WIPO Re. Application No. PCT/IL2018/050071. (10 Pages).
Notice of Grounds for Rejection dated Nov. 29, 2018 From the Korea Intellectual Property Office Re. Application No. 10-2014-7009267 and Its Translation Into English. (11 Pages).
Restriction Official Action dated Feb. 21, 2019 From the US Patent and Trademark Office Re. U.S. Appl. No. 15/744,905. (7 pages).
Examination Report Under Sections 12 & 13 of the Patents Act, 1970 and the Patents Rules, 2003 dated Jan. 10, 2019 From the Government of India, Intellectual Property India, Patents, Designs, Trade Marks, Geographical Indications Re. Application No. 577/MUMNP/2014. (7 Pages).
Advisory Action dated Jun. 2, 2020 from the US Patent and Trademark Office Re. U.S. Appl. No. 15/744,905. (3 pages).
Communication Pursuant to Article 94(3) EPC dated Apr. 24, 2020 From the European Patent Office Re. Application No. 16750269.9. (4 Pages).
Notice of Allowance dated May 14, 2020 from the US Patent and Trademark Office Re. U.S. Appl. No. 15/873,943. (74 pages).
Notice of Reasons for Refusal dated Jun. 9, 2020 From the Japan Patent Office Re. Application No. 2018-501339 and Its Translation Into English. (18 Pages).
Notification of Office Action dated Jun. 12, 2020 From the National Intellectual Property Administration of the People's Republic of China Re. Application No. 201610307275.9 and Its Translation Into English. (21 Pages).
Bachar-Lustig et al. "Next Generation Veto Cells for Non-Myeloablative Haploidentical HSCT: Combining Anti-Viral and Graft Facilitating Activity", Experimental Transplantation: Basic Biology, Pre-Clinical Models: Poster 2, Dec. 2, 2016.
Official Action dated Jan. 2, 2020 From the US Patent and Trademark Office Re. U.S. Appl. No. 15/825,275. (55 pages).
Communication Pursuant to Article 94(3) EPC dated Mar. 27, 2020 From the European Patent Office Re. Application No. 16745186.3. (7 Pages).
Official Action dated Apr. 21, 2020 from the US Patent and Trademark Office Re. U.S. Appl. No. 15/242,666. (20 pages).
"Generation of CD 19-Chimeric Antigen Receptor Modified CD8+ T Cells Derived from Virus-Specific Central Memory T Cells", Blood, The Journal of the American Society of Hematology,119(1): 72-82, Jan. 5, 2012.
Official Action dated Jan. 29, 2020 From the US Patent and Trademark Office Re. U.S. Appl. No. 15/744,905. (20 pages).
Figueroa et al. "Chimeric Antigen Receptor Engineering: A Right Step in the Evolution of Adoptive Cellular Immunotherapy", International Reviews of Immunology, 34:154-187, 2015.
Marcus et al. "Redirected Tumor-Specific Allogeneic T cells for Universal Treatment of Cancer", Blood, The Journal of the American Society of Hematology 118(4): 975-983, Jul. 28, 2011.

* cited by examiner

FIG. 9

| Day -2 | Day -1 | Day 0 | Every 3rd day |
|---|---|---|---|
| Injection of 0.25*10⁶ B16-OVA melanoma cells s.c. | TBI 6Gy C57BL/6 host | 1*10⁶ OT1-F1 (C57BL/6*Balb/c) CD8+ naïve T-cells ± 5*10⁶ F1 (C57BL/6*Balb/c) Tcm OR 5*10⁶ Allogeneic (Balb/c) Tcm | Tumor measure ± peripheral blood analysis |

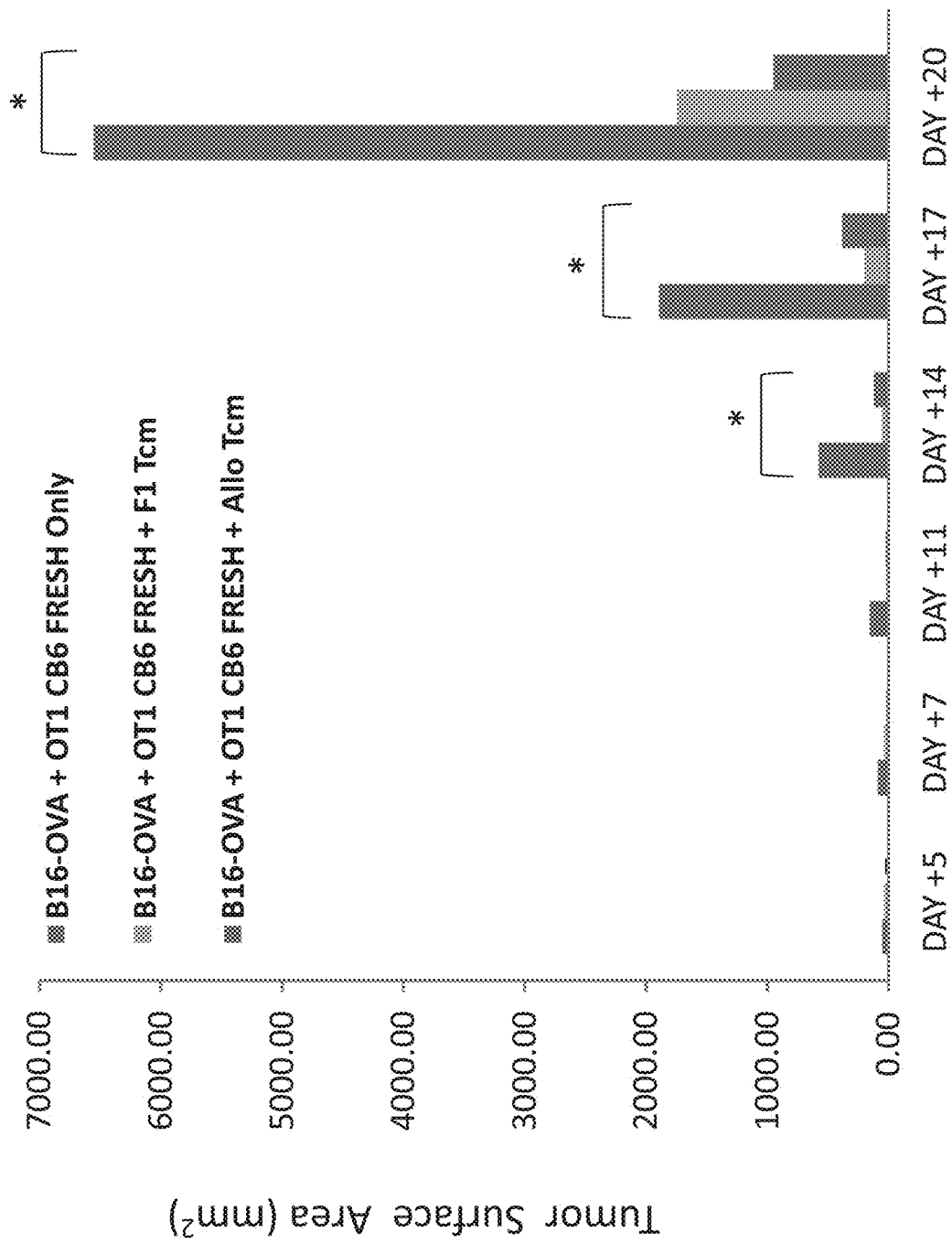

METHODS OF TRANSPLANTATION AND DISEASE TREATMENT

RELATED APPLICATIONS

This application is a National Phase of PCT Patent Application No. PCT/IL2016/050774 having International filing date of Jul. 14, 2016, which claims the benefit of priority under 35 USC § 119(e) of U.S. Provisional Patent Application Nos. 62/193,207 and 62/193,229 both filed on Jul. 16, 2015. The contents of the above applications are all incorporated by reference as if fully set forth herein in their entirety.

FIELD AND BACKGROUND OF THE INVENTION

The present invention, in some embodiments thereof, relates to the use of tolerance inducing anti-third party cells comprising central memory T-lymphocyte phenotype in adoptive cellular therapy.

Adoptive immunotherapies have been employed in which therapeutic lymphocytes (e.g. T cells) are administered to patients in order to treat viral infection or cancer. Examples of such immunotherapies include the graft versus leukemia (GVL) effect mediated by donor lymphocyte infusion (DLI) for treatment of hematopoietic cancer after allogeneic stem cell transplantation. An additional example includes the therapeutic infusion of ex-vivo expanded tumor infiltrating lymphocytes (TIL) in combination with lymphodepletion for the treatment of melanoma [Fujiwara H., Pharmaceuticals (2014) 7: 1049-1068].

Despite these successes, both DLI and TIL therapies have major drawbacks, DLI is usually associated with graft versus host disease (GVHD) while preparation of TIL for therapy is time and labor consuming and not always successful. The main challenge remains separation of the GVL effect from GVHD. Thus, currently most therapeutics employ autologous or HLA-identical cells.

Previous studies have substantiated that hematopoietic stem cells, namely, cells within the CD34+ fraction, are endowed with veto activity (e.g. donor cells which lead to apoptosis of host cells upon contact with same), thereby allowing them to induce tolerance when administered to hosts at high numbers i.e. "megadose" transplants [Gur et al., Blood (2005) 105:2585-2593; Gur et al., Blood (2002) 99:4174-4181; Rachamim et al., Transplantation (1998) 65:1386-1393]. However, the amount of $CD34^+$ cells that can be harvested in humans is usually insufficient for achieving tolerance under reduced intensity conditioning protocols (RIC).

Other cell types have also been shown to mediate veto activity including T lymphocytes (e.g. $CD8^+$ CTLs), natural killer cells and dendritic cells. Direct comparison of the veto activity of various cell types revealed that cytotoxic T lymphocytes (CTLs) comprise the strongest veto effect [Reich-Zeliger et al., J Immunol. (2004) 173:6654-6659].

One approach developed to generate veto CTLs devoid of graft versus host (GVH) activity was described by Reisner and co-workers, in which CTLs were stimulated against $3^{rd}$-party stimulators in the absence of exogenous IL-2. This approach was based on the observation that only activated cytotoxic T lymphocyte precursors (CTLp) were capable of surviving the IL-2 deprivation in the primary culture (IL-2 starvation results in apoptosis of non-induced T cells). This method was shown in vitro and in vivo to deplete GVH reactivity from the anti-$3^{rd}$ party veto CTLs [PCT Publication No. WO 2001/049243, Bachar-Lustig et al., Blood. 2003; 102:1943-1950; Aviner et al., Hum Immunol. (2005) 66:644-652]. Introduction of these anti-$3^{rd}$ party veto CTLs into a recipient (along with a transplant) prevented graft rejection without inducing graft versus host disease (GVHD) (PCT Publication No. WO 2001/049243).

Various approaches have been contemplated for generation of tolerance inducing cells devoid of GVH reactivity and the use of same as an adjuvant treatment for graft transplantation, some are summarized infra.

PCT Publication No. WO 2007/023491 discloses the use of tolerogenic cells for reducing or preventing graft rejection of a non-syngeneic graft in a subject. The tolerogenic T regulatory cells disclosed (e.g. $CD4^+CD25^+$ cells) may be derived from any donor who is non-syngeneic with both the subject and the graft ("third-party" tolerogenic cells). The graft (e.g. bone marrow) may be derived from any graft donor who is allogeneic or xenogeneic with the subject.

PCT Publication No. WO 2002/102971 discloses the use of cultured hematopoietic progenitor cells (HPC) comprising enhanced veto activity for inducing tolerance to a transplant transplanted from a donor to a recipient. The tolerogenic cells disclosed preferably express CD33 and are administered prior to, concomitantly with or following transplantation of the transplant (e.g. cell or organ transplant).

PCT Publication No. WO 2010/049935 discloses an isolated population of cells comprising non-GVHD inducing anti-third party cells having a central memory T-lymphocyte (Tcm) phenotype, the cells being tolerance-inducing cells and capable of homing to the lymph nodes following transplantation. Specifically, WO 2010/049935 teaches co-transplantation of immature hematopoietic stem cells along with the anti-third party Tcm cells. The use of the anti-third party Tcm cells enabled engraftment of immature hematopoietic cells without graft versus host disease (GVHD).

PCT Publication No. WO 2013/035099 discloses methods of generating an isolated population of cells comprising anti-third party cells having central memory a T-lymphocyte (Tcm) phenotype, the cells being tolerance-inducing cells and/or endowed with anti-disease activity, and capable of homing to the lymph nodes following transplantation.

SUMMARY OF THE INVENTION

According to an aspect of some embodiments of the present invention there is provided a method of transplantation, the method comprising administering to a subject in need of transplantation of cells in suspension, a therapeutically effective amount of anti-third party cells having a central memory T-lymphocyte (Tcm) phenotype, the anti-third party cells being tolerance-inducing cells and capable of homing to the lymph nodes following transplantation, wherein the cells in suspension comprise non-hematopoietic cells or hematopoietic cells which are not stem cells.

According to an aspect of some embodiments of the present invention there is provided a therapeutically effective amount of anti-third party cells having a central memory T-lymphocyte (Tcm) phenotype, the anti-third party cells being tolerance-inducing cells and capable of homing to the lymph nodes following transplantation, for use in treating a subject in need of transplantation of cells in suspension, wherein the cells in suspension comprise non-hematopoietic cells or hematopoietic cells which are not stem cells.

According to an aspect of some embodiments of the present invention there is provided a method of treating a disease in a subject in need thereof, the method comprising:

(a) administering to the subject a therapeutically effective amount of cells in suspension, wherein the cells in suspension comprise non-hematopoietic cells or hematopoietic cells which are not stem cells; and (b) administering to the subject a therapeutically effective amount of anti-third party cells having a central memory T-lymphocyte (Tcm) phenotype, the anti-third party cells being tolerance-inducing cells and capable of homing to the lymph nodes following transplantation, thereby treating the disease.

According to some embodiments of the invention, step (a) and step (b) are carried out concomitantly.

According to some embodiments of the invention, step (b) is carried out prior to step (a).

According to an aspect of some embodiments of the present invention there is provided a therapeutically effective amount of cells in suspension, wherein the cells in suspension comprise non-hematopoietic cells or hematopoietic cells which are not stem cells, and a therapeutically effective amount of anti-third party cells having a central memory T-lymphocyte (Tcm) phenotype, the anti-third party cells being tolerance-inducing cells and capable of homing to the lymph nodes following transplantation, for use in treating a disease in a subject in need thereof.

According to an aspect of some embodiments of the present invention there is provided a kit for transplantation comprising: (i) cells in suspension wherein the cells in suspension comprise non-hematopoietic cells or hematopoietic cells which are not stem cells; and (ii) anti-third party cells having a central memory T-lymphocyte (Tcm) phenotype, the anti-third party cells being tolerance-inducing cells and capable of homing to the lymph nodes following transplantation.

According to some embodiments of the invention, the cells are formulated for intravenous administration.

According to some embodiments of the invention, the method further comprises administering the cells in suspension to the subject.

According to some embodiments of the invention, the therapeutically effective amount of anti-third party cells for use further comprises a therapeutically effective amount of cells in suspension, wherein the cells in suspension comprise non-hematopoietic cells or hematopoietic cells which are not stem cells.

According to some embodiments of the invention, the non-hematopoietic cells comprise differentiated cells.

According to some embodiments of the invention, the differentiated cells are selected from the group consisting of pulmonary cells, pancreatic cells, nephric cells, hepatic cells, cardiac cells, brain cells, intestine cells, skin cells, spleen cells and ovarian cells.

According to some embodiments of the invention, the differentiated cells are obtained from a fetal tissue.

According to some embodiments of the invention, the differentiated cells are obtained from an adult tissue.

According to some embodiments of the invention, the non-hematopoietic cells comprise progenitor or stem cells.

According to some embodiments of the invention, the progenitor cells or stem cells are selected from the group consisting of mesenchymal stem cells, endothelial progenitor cells and epithelial progenitor cells.

According to some embodiments of the invention, the hematopoietic cells which are not stem cells comprise a subpopulation of lymphatic cells.

According to some embodiments of the invention, the hematopoietic cells which are not stem cells comprise immune cells.

According to some embodiments of the invention, the immune cells are selected from the group consisting of T cells, B cells, NK cells, NKT cells and dendritic cells (DCs).

According to some embodiments of the invention, the T cells are selected from the group consisting of CD4+ T cells, CD8+ T cells, tumor infiltrating lymphocytes (TIL) and tumor-associated lymphocytes (TALs).

According to some embodiments of the invention, the non-hematopoietic cells or hematopoietic cells which are not stem cells are genetically modified.

According to some embodiments of the invention, the genetically modified cells comprise genetically modified immune cells.

According to some embodiments of the invention, the immune cells express a chimeric antigen receptor (CAR) or a modified T cell receptor (TCR).

According to some embodiments of the invention, the immune cells are T cells.

According to some embodiments of the invention, the administering to the subject a therapeutically effective amount of the anti-third party cells having the Tcm phenotype is effected at least twice.

According to some embodiments of the invention, the subject in need of transplantation has a malignant disease.

According to some embodiments of the invention, the disease is a malignant disease.

According to some embodiments of the invention, the malignant disease is a solid tumor or tumor metastasis.

According to some embodiments of the invention, the malignant disease is a hematological malignancy.

According to some embodiments of the invention, the malignant disease is selected from the group consisting of a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer and a pancreatic cancer.

According to some embodiments of the invention, the subject in need of transplantation has a non-malignant disease.

According to some embodiments of the invention, the disease is a non-malignant disease.

According to some embodiments of the invention, the non-malignant disease is selected from the group consisting of an organ dysfunction or failure, an infectious disease, an autoimmune disease and an injury.

According to some embodiments of the invention, the non-malignant disease is selected from the group consisting of a Parkinson's disease, an Alzheimer's disease, a multiple sclerosis, a retinal disease, a diabetes mellitus, a cerebral ischemia, a myogenic disease, a pulmonary disease, a renal disease, a hepatic disease, a cardiac disease, a gastrointestinal tract disease, a skin disease, a fertility disease and a brain disease.

According to some embodiments of the invention, when the progenitor cells are mesenchymal stem cells the disease is a medical condition selected from the group consisting of a cosmetic condition, a tissue or organ damage, an orthopedic condition, a neural condition, a heart disease or condition, a diabetes, a deafness, a Crohn's disease, an autoimmune disorder, a leukemia, a cancer, a sickle cell disease, an amyotrophic lateral sclerosis and a metabolic disorders.

According to some embodiments of the invention, when the progenitor cells are endothelial progenitor cells the disease is a medical condition selected from the group consisting of a bone disease, a bone damage, a cardiovascular disease, a cardiovascular injury, an ischemic disease, an ischemic injury, a vascular disease, a sickle cell disease, an atherosclerosis, a diabetes and an autoimmune disorder.

According to some embodiments of the invention, when the progenitor cells are epithelial progenitor cells the disease is a medical condition selected from the group consisting of a ulcer, an inflammatory bowel disease (IBD), a Crohn's disease, an ulcerative colitis, an Alzheimer's disease, a wound healing defect, a cancer, a chronic obstructive pulmonary disease (COPD), a pulmonary fibrosis, an idiopathic pulmonary fibrosis, a pulmonary hypertension, a lung cancer, a sarcoidosis, an acute lung injury (adult respiratory distress syndrome), a respiratory distress syndrome of prematurity, a chronic lung disease of prematurity (bronchopulmonary dysplasia), a surfactant protein B deficiency, a congenital diaphragmatic hernia, a pulmonary alveolar proteinosis, a pulmonary hypoplasia, a lung injury and a corneal degeneration.

According to some embodiments of the invention, when the hematopoietic cells which are not stem cells comprise immune cells the disease is a medical condition selected from the group consisting of a malignancy, an autoimmune disease and an infectious disease.

According to some embodiments of the invention, the non-hematopoietic cells or hematopoietic cells which are not stem cells are non-syngeneic with the subject.

According to some embodiments of the invention, the non-hematopoietic cells or hematopoietic cells which are not stem cells and the anti-third party cells having the Tcm phenotype are obtained from the same donor.

According to some embodiments of the invention, the anti-third party cells having the Tcm phenotype are syngeneic with the subject.

According to some embodiments of the invention, the anti-third party cells having the Tcm phenotype are non-syngeneic with the subject.

According to some embodiments of the invention, the anti-third party cells having the Tcm phenotype comprise a $CD3^+$, $CD8^+$, $CD62L^+$, $CD45RA^-$, $CD45RO^+$ signature.

According to some embodiments of the invention, at least 50% of the isolated population of cells are CD3+CD8+ cells of which at least 50% have the signature.

According to some embodiments of the invention, the method further comprises conditioning the subject under sublethal, lethal or supralethal conditioning protocol prior to the administering.

According to some embodiments of the invention, the therapeutically effective amount of cells for use further comprises a sublethal, lethal or supralethal conditioning protocol.

According to some embodiments of the invention, the sublethal, lethal or supralethal conditioning is selected from the group consisting of a total body irradiation (TBI), a partial body irradiation, a myeloablative conditioning, a non-myeloablative conditioning, a co-stimulatory blockade, a chemotherapeutic agent and an antibody immunotherapy.

According to some embodiments of the invention, the sublethal conditioning protocol is selected from the group consisting of a total body irradiation (TBI), a co-stimulatory blockade, a chemotherapeutic agent and an antibody immunotherapy.

According to some embodiments of the invention, the administering is effected by a route selected from the group consisting of intratracheal, intrabronchial, intraalveolar, intravenous, intraperitoneal, intranasal, subcutaneous, intramedullary, intrathecal, intraventricular, intracardiac, intramuscular, intraserosal, intramucosal, transmucosal, transnasal, rectal and intestinal.

According to some embodiments of the invention, the cells are formulated for administration by a route selected from the group consisting of intratracheal, intrabronchial, intraalveolar, intravenous, intraperitoneal, intranasal, subcutaneous, intramedullary, intrathecal, intraventricular, intracardiac, intramuscular, intraserosal, intramucosal, transmucosal, transnasal, rectal and intestinal.

According to some embodiments of the invention, the subject is a human subject.

According to some embodiments of the invention, the anti-third party cells having the Tcm phenotype are generated by a method comprising: (a) contacting peripheral blood mononuclear cells (PBMCs) with a third party antigen or antigens in the presence of IL-21 so as to allow enrichment of antigen reactive cells; and (b) culturing the cells resulting from step (a) in the presence of IL-21, IL-15 and IL-7 so as to allow proliferation of cells comprising the central memory T-lymphocyte (Tcm) anti-third party phenotype, thereby generating the anti-third party cells having the Tcm phenotype.

According to some embodiments of the invention, the method further comprises depleting adherent cells from the PBMCs prior to the contacting with the third party antigen or antigens.

According to some embodiments of the invention, the method further comprises depleting CD4+ and/or CD56+ cells from the PBMCs prior to the contacting with the third party antigen or antigens.

According to some embodiments of the invention, the method comprises selecting for activated cells following step (a) and prior to step (b).

According to some embodiments of the invention, the selecting for activated cells is effected by selection of CD137+ and/or CD25+ cells.

According to some embodiments of the invention, the third party antigen or antigens comprise dendritic cells.

According to some embodiments of the invention, the third party antigen or antigens is selected from the group consisting of third party cells, a cell antigen, a viral antigen, a bacterial antigen, a protein extract, a purified protein and a synthetic peptide presented by autologous presenting cells, non-autologous presenting cells or on an artificial vehicle or on artificial antigen presenting cells.

According to some embodiments of the invention, the third party cells are stimulatory cells selected from the group consisting of cells purified from peripheral blood lymphocytes, spleen or lymph nodes, cytokine-mobilized PBLs, in vitro expanded antigen-presenting cells (APC), in vitro expanded dendritic cells and artificial antigen presenting cells.

According to some embodiments of the invention, the anti-third party cells having the Tcm phenotype are generated by a method comprising: (a) treating non-adherent peripheral blood mononuclear cells (PBMCs) with an agent capable of depleting CD4+ and/or CD56+ cells so as to obtain CD8+ T cells; (b) contacting the CD8+ T cells with third party dendritic cells in the presence of IL-21 for 12 hours to 5 days so as to allow enrichment of antigen reactive cells; (c) culturing the cells resulting from step (b) in the presence of IL-21, IL-15 and IL-7 for 5-20 days so as to allow proliferation of cells comprising the central memory T-lymphocyte (Tcm) phenotype, thereby generating the isolated population of cells.

According to some embodiments of the invention, the method further comprises culturing the cells resulting from step (b) with the third party dendritic cells in the presence of IL-21, IL-15 and IL-7 for 12 hours to 3 days prior to step (c).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A, 1B and 1C are schematic illustrations of models for studying the ability of Tcm cells to induce tolerance in the absence of the inducive properties of allogeneic BM. Tcm cell survival and proliferation was analyzed via FACS while downregulation of host CTL activity by Tcm cells was tested using $^{51}$Cr assay.

Figure 1A:
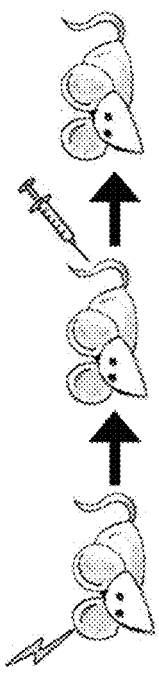
Figure 2B:
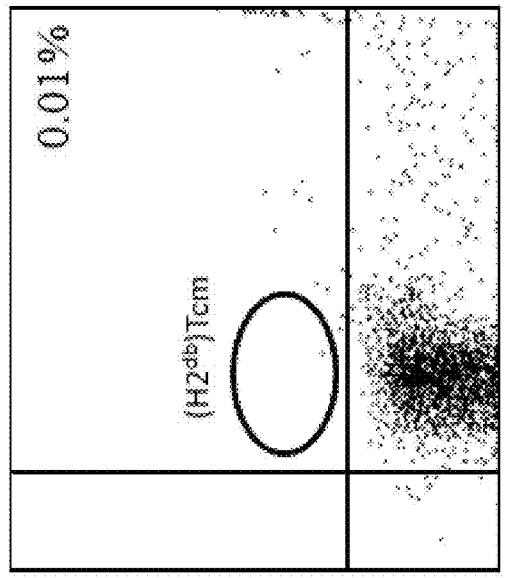
Figure 2A:
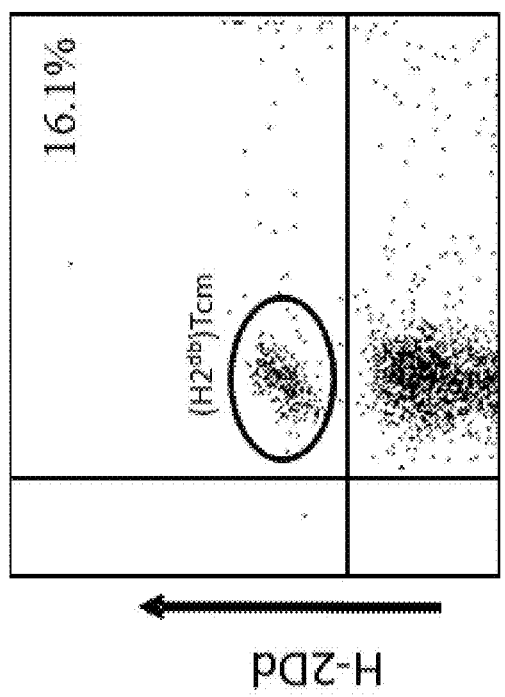

FIGS. 2A-B are graphs illustrating the persistence of adoptively transferred F1-Tcm cells under syngeneic bone marrow transplant (BMT) settings. C57BL/6 (H-2b) mice were transplanted as outlined in FIG. 1A. Representative scatter plot of one mouse in each group, showing percentage of Tcm cells in peripheral whole blood of mice, analyzed 60 days post-transplant by FACS using $\alpha H2D^d$ (Donor) and $\alpha H2K^b$ to identify F1($H2D^d \times H2K^b$)-Tcm cells.

Figure 3:
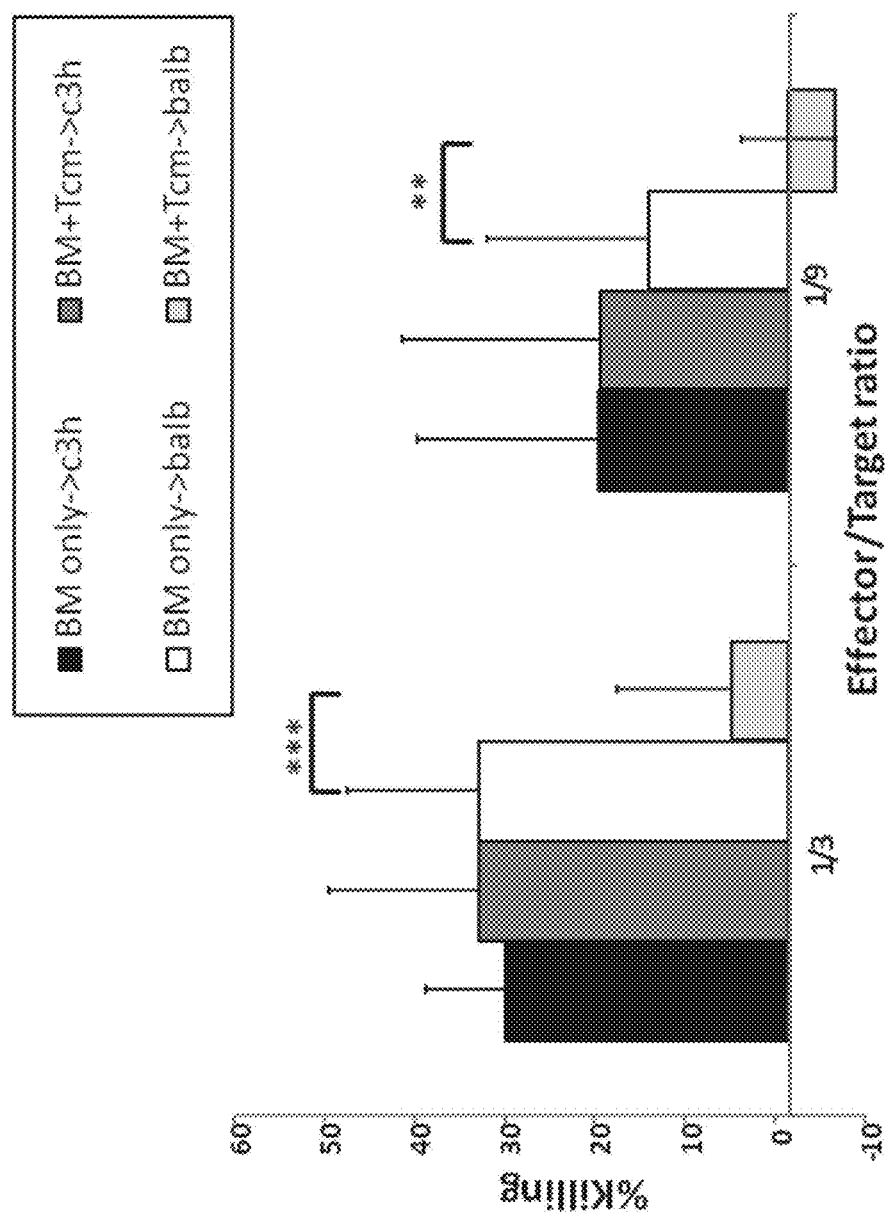

FIG. 3 is a graph illustrating that Tcm cells specifically delete anti-donor T cells from a polyclonal Host T-cell (HTC) population, whilst sparing other HTCs to display cytotoxic activity. Mice were transplanted as outlined in FIG. 1A. Sixty days post transplantation mice were sacrificed, spleens and lymph nodes (LNs) were harvested and cells were selected for CD8+ (and negatively selected for H-2D$^d$ to exclude Tcm). These naive HTC were tested for their killing ability of either C3H (H-2$^k$) or BALB/c (H-2$^d$) targets in a chromium release assay. Bars display killing effect as follows: Killing of C3H target by HTC from mice receiving only BM (black bars, "BM only→C3H") or by cells from mice receiving also Tcm (dark grey bars, "BM+Tcm only→C3H"), or Killing of BALB/c target by HTC from mice receiving only BM (white bars, "BM only→BALB") or by T cells from mice receiving also Tcm (bright grey bars, "BM+Tcm→BALB"). Results are presented as mean±SD of percent killing from 12 wells for each group. Representative experiment out of 2 independent experiments performed is displayed. () Represents p-value of less than 0.01, (*) Represents p-value of less than 0.001.

Figure 4:
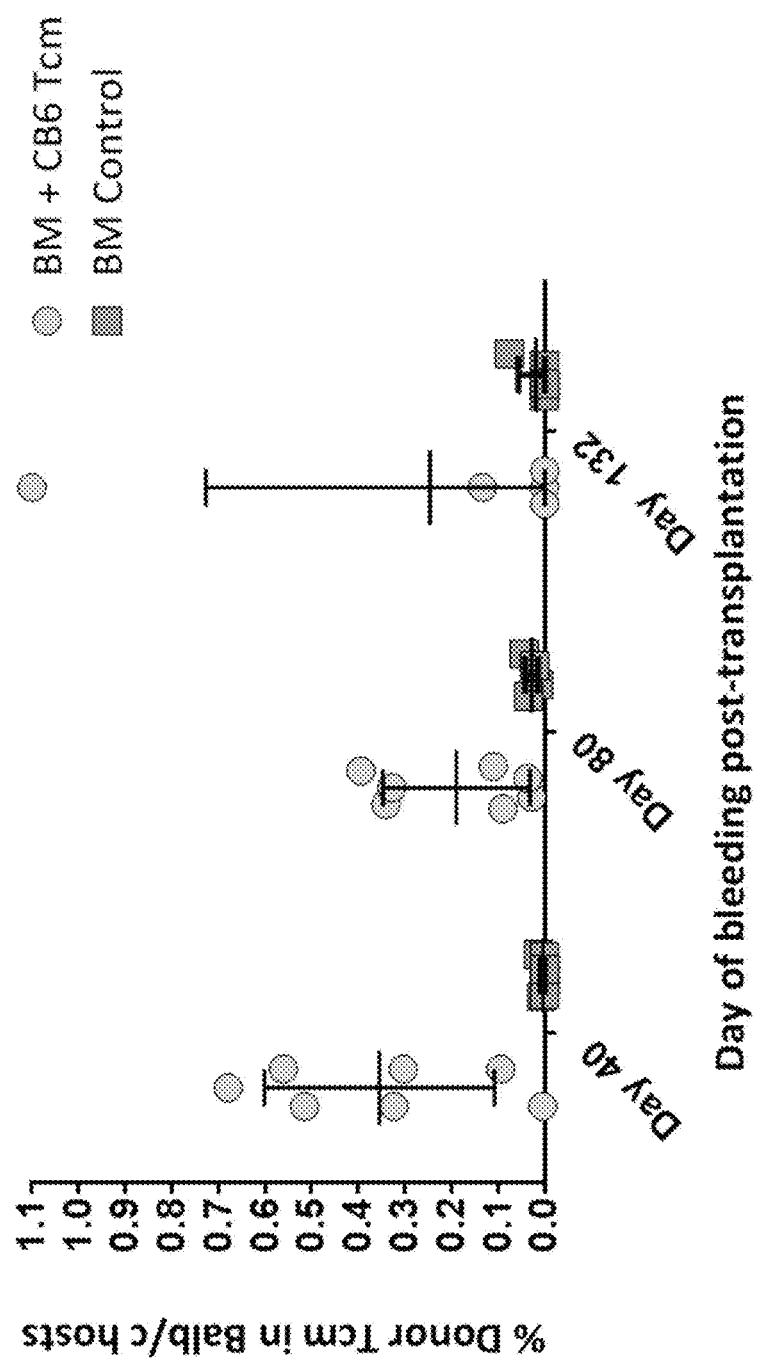

FIG. 4 is a graph illustrating that CB6 F1 derived Tcm cells persist in mice that received sub-lethal 5.5 Gy TBI with syngeneic T cell depleted bone marrow (TDBMT). Balb/c (H2D$^d$) mice were sub-lethally (5.5 Gy) irradiated and transplanted as described in FIG. 1B. Peripheral blood was analyzed 40, 80 and 132 days post-transplant by FACS using $\alpha H2D^d$ (Host) and $\alpha H2K^b$ to identify H2$^{db}$ F1-Tcm cells. Scatter plot showing the percentage of CB6 Tcm cells in each mouse, each dot represents the Tcm cell population in one mouse belonging to the appropriate group, showing the mean and SD of each group.

Figure 5:
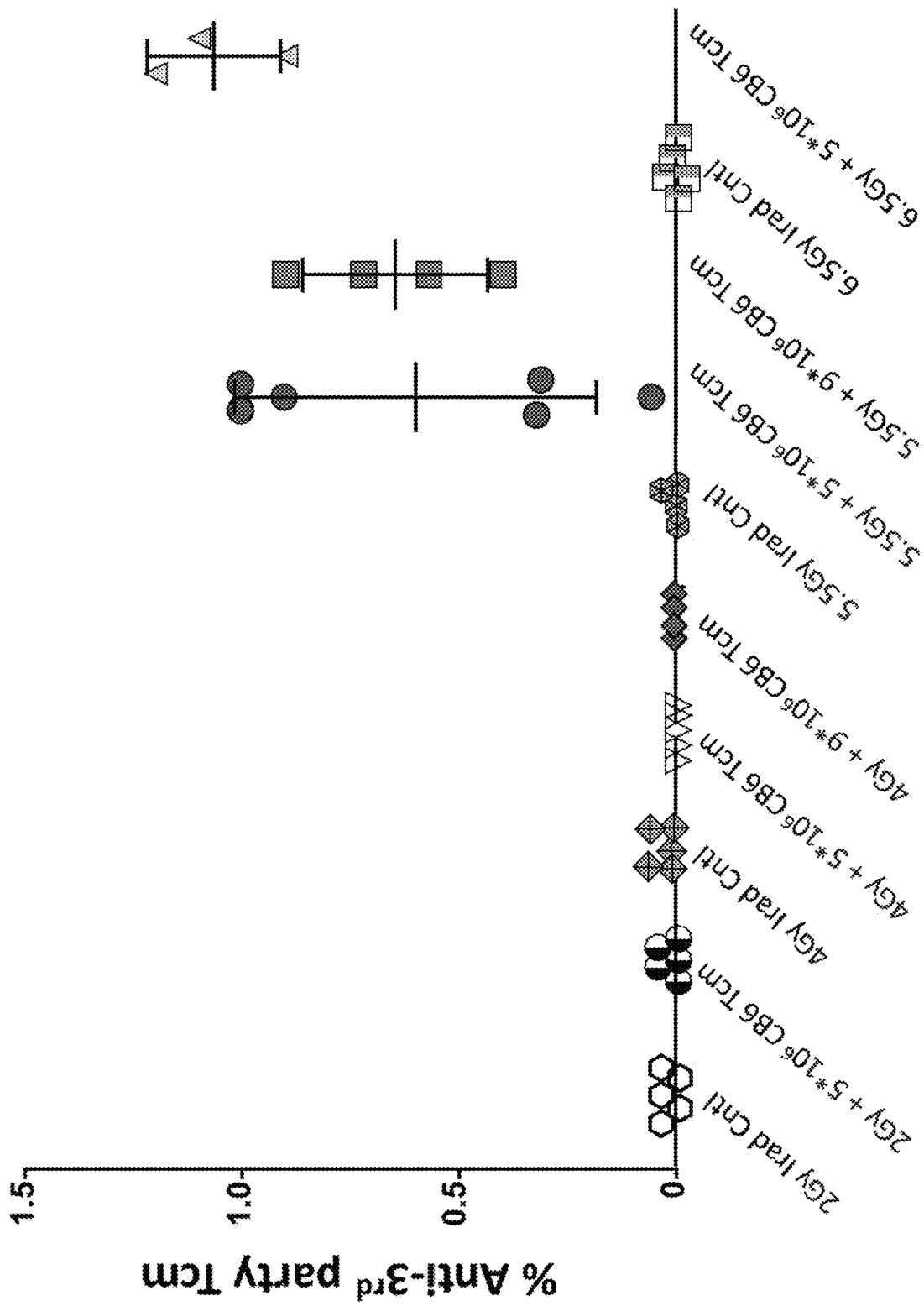

FIG. 5 is a graph illustrating calibration of irradiation dose allowing for Tcm cell survival without TDBMT. Balb/c (H2D$^d$) mice were sub-lethally irradiated with 2/4/5.5/6.5 Gy on day −1. On day 0 mice received 5×10$^6$ or 9×10$^6$ F1 CB6 (H-2$^{db}$) Tcm cells adoptively transferred to the tail vein of the mice. Scatter plot depicting percentage of CB6 Tcm cells in peripheral whole blood of Balb/c host mice, analyzed 42 days post-transplant by FACS using $\alpha H2D^d$ (Host) and $\alpha H2K^b$ to identify H2$^{db}$ F1-Tcm cells. Mean and SD are or each group are shown.

Figure 6B:
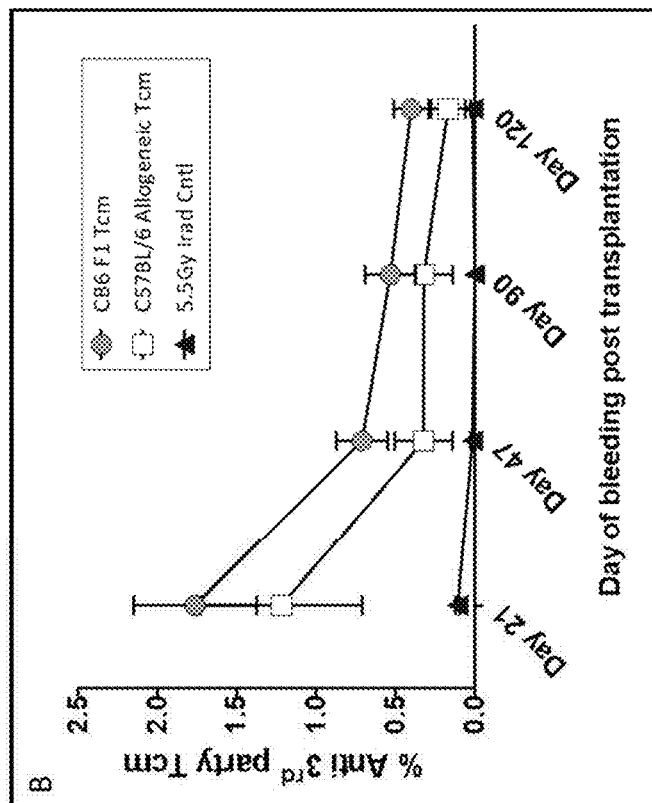
Figure 6A:
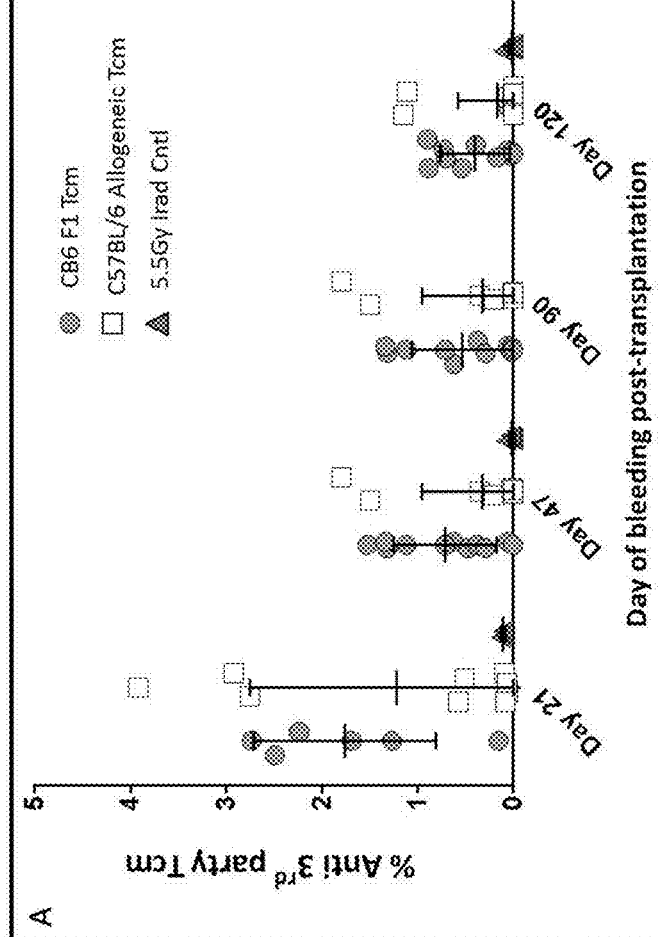

FIGS. 6A-B are graphs illustrating that fully-allogeneic Tcm cells persist in 5.5 Gy Balb/c mice for a prolonged period. Balb/c (H-2$^d$) mice were transplanted as outlined in FIG. 1C. Tcm cells were of CB6-F1 (H-2$^{db}$) or C57BL/6 (H-2$^b$) origin. Mice were bled on the indicated days and the Tcm cell population was analyzed by FACS using $\alpha H2D^d$ (Host) and $\alpha H2K^b$ (Donor) to identify H2$^{db}$ F1-Tcm and H2$^b$ Allo-Tcm cells. FIG. 6A is a scatter plot depicting the percentage of Tcm cells in Balb/c hosts. Each dot represents the Tcm cell population in one mouse belonging to the appropriate group, showing the mean and SD of each group. FIG. 6B is a time curve graph illustrating decrease in Tcm cell population in peripheral blood from over a prolonged period of time.

Figure 7:
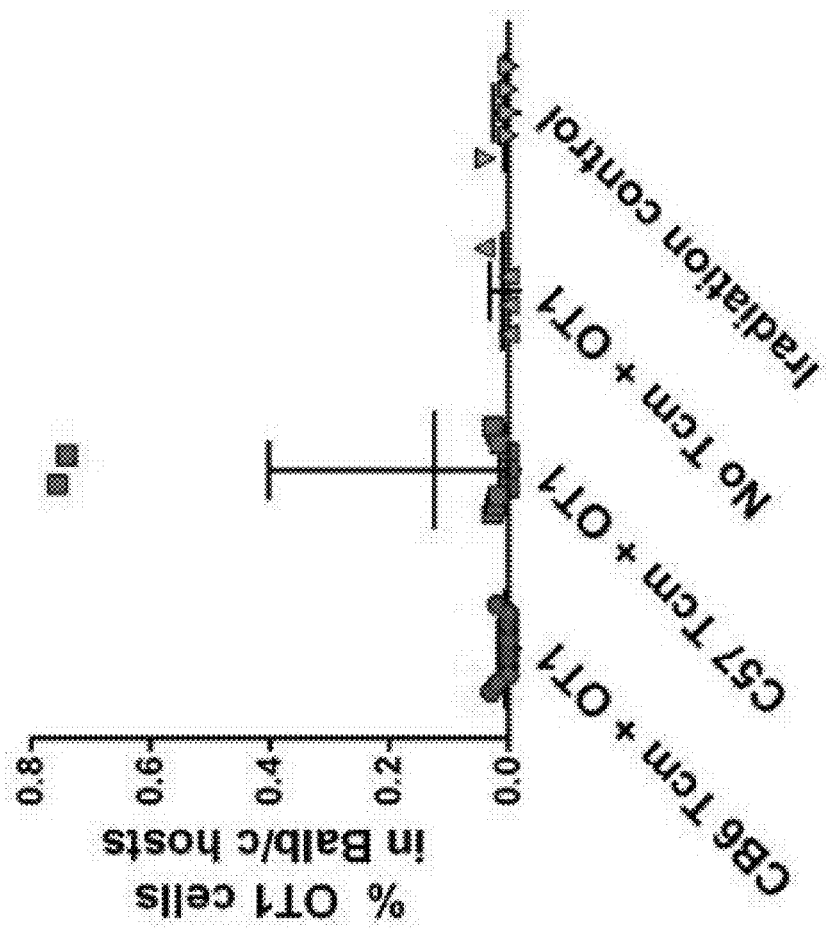

FIG. 7 is a graph illustrating that fully-allogeneic Tcm cells persist in 5.5 Gy Balb/c mice and facilitate engraftment of additional donor T cells. Balb/c (H-2$^d$) mice received 5.5 Gy TBI on day −1, and 5×10$^6$ CB6 (H-2$^{db}$) or C57BL/6(H-2$^b$) derived Tcm cells on day 0. 89 days post Tcm cell injection, the mice were irradiated with 2 Gy TBI, the following day they received 2×10$^6$ CD45.1$^+$, OT1$^+$, RAG$^+$ CD8+ cells. Scatter plot showing bleeding on day 120 post Tcm cell transplantation and 30 days post OT-1 cells transplantation.

Figure 8:
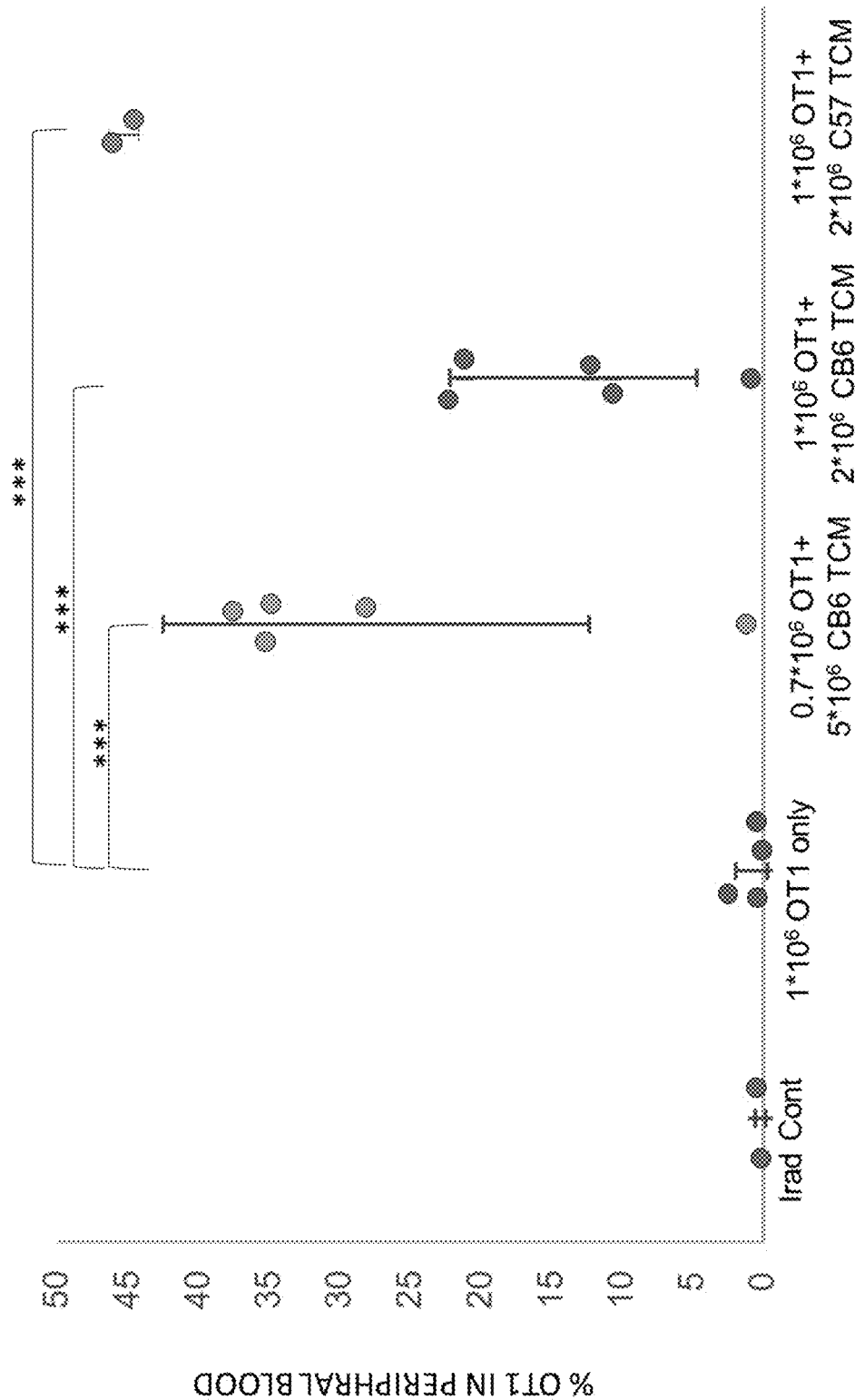

FIG. 8 is a graph illustrating an analysis of OT-1 cells in the peripheral blood of sublethally irradiated Balb/c mice. Balb/c (H-2$^d$) mice received 5.25 Gy TBI on day −1, and proceeded to receive naive CD8$^+$ OT-1$^+$CD45.1$^+$RAG$^-$ cells on day 0, with or without the CB6 (H-2$^{db}$) or C57BL/6 (H-2$^b$) derived Tcm cells at the indicated numbers. Sixty days post Tcm cell injection peripheral blood of the mice was tested to detect the presence of OT-1 cells using FACS analysis. Scatter plot showing the percentage of OT-1 cells of different groups out of the total CD8$^+$H-2$^{b+}$ cells.

FIG. 9 is a graph illustrating a B16-melanoma residual disease prevention model. In this model, B16-OVA expressing melanoma cells were injected (on day −2) into C57BL/6 mice. The following day (day −1), these mice were treated by RIC with TBI. The following day (day 0), tumor bearing C57BL/6 mice were administered OT1-F1 (H-2$^{db}$) fresh cells alone or concomitantly with F1 Tcm cells (i.e. from the same cell donor) or with allogeneic Balb/c Tcm cells expressing the non-shared MHC (H-2$^d$) of the OT1-F1 cells.

FIG. 10 is a graph illustrating that anti-third party Tcm cells support engraftment of mis-matched anti-Ova transgenic donor-derived CD8+ cells (OT1-F1) by virtue of veto activity and enable efficient eradication of Ova-bearing melanoma tumor cells.

DESCRIPTION OF SPECIFIC EMBODIMENTS OF THE INVENTION

The present invention, in some embodiments thereof, relates to the use of tolerance inducing anti-third party cells comprising central memory T-lymphocyte phenotype in adoptive cellular therapy.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cell-based therapies with various lymphocytes and antigen-presenting cells are promising approaches for immunotherapy. Adoptive cell transfer (ACT), including transfer of immune-derived cells, from an autologous or non-autologous source offers the goal of transferring the immunologic functionality and characteristics into the new host. In order to minimize graft rejection and GVHD, autologous cells are usually employed. Alternatively, bone marrow depleted of T cells is transplanted together with veto cells in order to avoid graft rejection and GVHD. Another method previously employed for ACT comprises genetically modified T cells, wherein the specificity of the cells is redirected towards the target antigen. However, graft rejection is still a major concern in adoptive cell transfer therapy.

While reducing the present invention to practice, the present inventors have surprisingly uncovered that anti-third party Tcm cells are equipped with their own veto abilities and can induce tolerance on their own for transplantation of various types of cells in suspension, even in the absence of hematopoietic CD34+ stem cells. Thus, the Tcm cells of the invention can assist transplantation of various types of non-hematopoietic cells or hematopoietic cells which are not stem cells in the absence of graft rejection and/or graft versus host disease.

As is shown herein below and in the Examples section which follows, the present inventors have shown that allogeneic donor type anti-third party Tcm cells can survive in a host for a prolonged time with or without a concomitant bone marrow transplant (e.g. more than 120 days, FIGS. 2A-B and FIGS. 6A-B, respectively). Moreover, the anti-third party Tcm cells exerted veto activity (FIG. 3). Thus, application of anti-third party Tcm cells alone even in the absence of BM precursors could offer a useful tool for creating a time-window of opportunity for administration of cell therapy (i.e. a period of time in which the anti-third party cells survive and exert their veto activity enabling for the adoptive cells to exert their function), utilizing donor-type cells specific for tumor antigens, pathogens and self-antigens.

Taken together, these results substantiate the use of anti-third party Tcm cells as tolerance inducing cells for adoptive cell transfer and for use in disease treatment in situations in which adoptive cell therapy warranted including in cancer therapy and in therapy of viral diseases.

The phrase "cells in suspension" as used herein, refers to cells which have been isolated from their natural environment (e.g., the human body) and are extracted from the blood or tissue/organ while maintaining viability but do not maintain a tissue structure (i.e., no vascularized tissue structure) such that they may be injectable such as by intravenous administration. According to a specific embodiment the cells in suspension are not attached to a solid support.

As used herein, the term "non-hematopoietic cells" refers to bodily cells which are not of the hematopoietic lineage. Such cells include differentiated cells as well as progenitor cells and stem cells.

As used herein, the phrase "differentiated cells" refers to terminally differentiated cells. Exemplary cells which may be transplanted according to the present teachings include, but are not limited to, liver, pancreas, spleen, kidney, heart, lung, skin, intestine, fallopian tubes, ovarian or brain cells.

According to one embodiment, the differentiated cells are obtained from an adult tissue (i.e. a tissue of an organism at any time after birth).

According to one embodiment, the differentiated cells are obtained from a fetal tissue (as described in detail herein-below).

According to one embodiment of the invention, the non-hematopoietic cells comprise progenitor or stem cells.

As used herein, the phrase "stem cells" refers to cells which can differentiate into other cell types having a particular, specialized function (e.g., fully differentiated cells). Examples include but are not limited to totipotent, pluripotent, or multipotent cells.

The totipotent stem cells give rise to "progenitor cells" more differentiated than the totipotent cells. These cells are capable of differentiating into specific cell lineages, e.g. endothelial lineage, epithelial lineage or mesenchymal lineage.

As used herein, the term "endothelial progenitor cells" or "EPCs" refers to undifferentiated cells committed to endothelial lineage. EPCs have the capacity to proliferate, migrate, and differentiate into endothelial cells but have not yet acquired characteristics of mature endothelial cells. EPCs include but are not limited to colony forming unit-endothelial cells (CFU-ECs), circulating angiogenic cells (CACs), circulating endothelial precursors (CEPs), and endothelial colony-forming cells (ECFC) including low proliferative potential ECFC (LPP-ECFC) and/or high proliferative ECFC (HPP-ECFC).

EPCs can be isolated from blood, bone marrow, or cord blood and can be identified in the CD34+ cell fraction in adult human peripheral mononuclear cells. EPCs may also be mobilized from bone marrow into peripheral blood (circulating EPCs) in response to certain physiological stimuli, such as, for example, tissue injury. Circulating EPCs can be obtained from adult human blood. In certain aspects, EPCs can be isolated from these or other sources using CD34+ cells or CD133+ cells alone or in combination with KDR+ as an EPC-rich cell fraction in peripheral blood via direct FACS sorting or other available ex-vivo selection method such as magnetic beads, microfluidics, lab-on-a-chip, affinity column or associated device.

As used herein, the term "epithelial progenitor cells" refers to undifferentiated cells committed to epithelial lineage. Epithelial progenitor cells have the capacity to proliferate, migrate, and differentiate into epithelial cells but have not yet acquired characteristics of mature epithelial cells. Epithelial cells make up the tissues which line any of the cavities or surfaces of structures throughout the mammalian body. Epithelial progenitor cells include, but are not limited to, lung, gastrointestinal tract, reproductive organ, urinary tract, renal, skin, ischemic, cardiac, endothelial, circulatory and brain epithelial progenitor cells. In certain aspects, epithelial progenitor cells can be identified by expression of cell markers e.g. CD34, CD105, HES1, FRZB1, DCT, SOD2, ABCG2, CDH1 and/or KRT19.

Epithelial progenitor cells can be isolated from tissues (e.g. pancreatic, pulmonary, renal, cardiac etc.), such as from fetal tissues, by any method known to one of skill in the art, e.g. by microdissection. Non-limiting examples of microdissection include devices that render mechanical shearing forces (i.e. homogenizer, mortar and pestle, blender, etc.), devices that render cuts or tears (i.e. scalpel, syringes, forceps, etc.), or ultrasonic devices. Alternatively, another method of microdissecting tissues is the use of enzyme treatment. Various enzyme treatments used to microdissect tissues are known to one of skill in the art, such as but not limited to, the use of collagenase, as described in further detail hereinbelow.

As used herein "mesenchymal stem cells", "MSCs", "stromal stem cells" or "stromal cells" which are used herein interchangeably, refer to adherent cells having a stromal stem cell phenotype. The cells typically originate from bone marrow, adipose tissue or placenta, though other organs of the body comprise these cells as well.

A stromal stem cell phenotype includes, for example, a spindle shape. Alternatively or additionally the cells may express at least one surface marker or a collection of surface markers (e.g. surface marker) typical to mesenchymal/stromal stem cells. Examples of stromal stem cell surface markers (positive and negative) include but are not limited to CD105+, CD29+, CD44+, CD73+, CD90+, CD34−, CD45−, CD80−, CD19−, CD5−, CD20−, CD11B−, CD14−, CD19−, CD79−, HLA-DR−, and FMC7−. Other mesenchymal stem cell markers include but are not limited to tyrosine hydroxylase, nestin and HNF-4α.

Expression of any of these markers may be determined at the mRNA or protein levels using methods known in the art such as by using hybridization-based techniques e.g., Northern blot, Fluorescent in situ hybridization, Reverse transcription PCR or an antibody to the at least one cell surface marker e.g., coupled directly or indirectly to a detectable moiety and analyzed by well known methods such as FACS, ELISA or Western blotting.

Examples of functional phenotypes typical of stromal stem cells include, but are not limited to, immune (T cell) suppression activity, hematopoietic stem cell support activity, as well as adipogenic, hepatogenic, osteogenic and neurogenic differentiation.

Any of these structural or functional features can be used to qualify the cells of the present invention.

MSCs which may be administered in accordance with this aspect of the present invention include cultured cells (in either two-dimensional or three-dimensional settings), harvested MSCs, as well as mesenchymal and partially or terminally differentiated derivatives of same.

The cells may be naive or genetically modified such as to derive a lineage of interest (see U.S. Patent Application No. 20030219423 or www(dot)jeccr(dot)com/content/34/1/33).

As used herein, the term "hematopoietic cells which are not stem cells" refers to all bone marrow-derived cells which circulate in the blood or lymphatic systems. This term refers to mature cell types and their immature precursors. Hematopoietic cells are typically identified by morphology and/or by expression of cell surface markers.

Hematopoietic cells which are not stem cells are typically sub-grouped into myeloid cells (e.g., neutrophils, eosinophils, basophils, mast cells, dendritic cells, monocytes and macrophages), lymphoid cells (e.g. B-cells, T-cells, NK-cells), erythrocytes and thrombocytes.

Thus, according to one embodiment, the cells are a subpopulation of lymphatic cells. Such cells include any cells which circulate in the lymphatic systems (e.g. in the bone marrow and thymus) including e.g. B-cells and T-cells.

According to one embodiment, the hematopoietic cells which are not stem cells comprise differentiated cells. Exemplary cells which may be transplanted according to the present teachings include, but are not limited to, immune cells (e.g. T cells, B cells, dendritic cells (DCs), natural killer cells (NK) and/or NKT cells). As used herein, the term "T cells" refers to differentiated lymphocytes with a $CD3^+$, T cell receptor $(TCR)^+$ having either $CD4^+$ or $CD8^+$ phenotype. The T cells may be effector T cells or a regulatory T cells.

As used herein, the term "effector T cells" refers to T cells that activate or direct other immune cells e.g. by producing cytokines or having a cytotoxic activity e.g., CD4+, Th1/Th2, CD8+ cytotoxic T lymphocyte (CTLs).

As used herein, the term "regulatory T cells" or "Tregs" refers to T cells that negatively regulate the activation of other T cells, including effector T cells, as well as innate immune system cells. Treg cells are characterized by sustained suppression of effector T cell responses. According to a specific embodiment, the Tregs are CD4+CD25+Foxp3+ T cells.

According to specific embodiments, the differentiated cells are T cells.

According to another specific embodiment, the T cells are CD8+ T cells.

According to another specific embodiment, the T cells are CD4+ T cells.

According to another specific embodiment, the T cells are naïve T cells (e.g. mature T cells which have not encountered its cognate antigen).

T cells according to the present method can be selected or modified to target a specific antigen (also termed adoptive cell therapy).

According to one embodiment, the T cells are natural anti-tumor or anti-viral T cells.

According to another specific embodiment, the T cells are tumor infiltrating lymphocytes (TILs). TILs can be isolated from a tumor mass (e.g. melanoma or renal cancer), e.g. following removal thereof from a subject, the cells can be expanded ex-vivo (e.g. using cytokines) and administered back to the subject for anti-cancer therapy.

According to another specific embodiment, the T cells are tumor-associated lymphocytes (TALs). TALs can be selected for T-cell receptor (TCR) specificity (see e.g. Cancer Immunol Immunother. 2009; 58: 553-66). In such cases, T cells are activated and expanded ex-vivo by incubation with tumor antigens (e.g. using antigen presenting cells such as mature DCs, B cells or by soluble peptides, artificial presenting cells, antigen coated beads, fresh cells, tumor cells or cell lines) preloaded with tumor antigens or transfected with mRNA or DNA coding for cancer antigens. T cells (e.g. CD8+ or CD4+ T cells) selected for TCR specificity against the tumor antigens are then administered to a subject for anti-cancer therapy.

According to one embodiment, the T cells (i.e. differentiated T cells) are genetically modified (as described in further detail below).

As used herein the term "B cells" refers to differentiated lymphocytes with a B cell receptor (BCR)+, CD19+ and/or B220+ phenotype. B cells are characterized by their ability to bind a specific antigen and elicit a humoral response (e.g. antibody secreting cells).

As used herein the terms "natural killer cells" or "NK cells" refer to differentiated lymphocytes with a CD16+ CD56+ and/or CD57+ TCR− phenotype. NK cells are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release cytokines that stimulate or inhibit the immune response.

As used herein the term "NKT cells" refers to a specialized population of T cells that express a semi-invariant $\mu\beta$ T-cell receptor, but also express a variety of molecular markers that are typically associated with NK cells, such as NK1.1. NKT cells include NK1.1$^+$ and NK1.1$^-$, as well as CD4$^+$, CD4$^-$, CD8$^+$ and CD8$^-$ cells. The TCR on NKT cells is unique in that it recognizes glycolipid antigens presented by the MHC I-like molecule CD1d. NKT cells can have either protective or deleterious effects due to their abilities to produce cytokines that promote either inflammation or immune tolerance.

As used herein the terms "dendritic cells" or "DCs" refer to antigen presenting cells capable of sensitizing HLA-restricted T cells. DCs include DCs derived from bone marrow hematopoietic cells such as plasmacytoid dendritic cells, myeloid dendritic cells, Langerhans cells and interdigitating cells; and follicular DCs. Dendritic cells may be recognized by function, or by phenotype, particularly by cell surface phenotype. These cells are characterized by their distinctive morphology having veil-like projections on the cell surface, intermediate to high levels of surface HLA-class II expression and ability to present antigen to T cells, particularly to naive T cells (See Steinman R, et al., Ann. Rev. Immunol. 1991; 9:271-196). Typically, cell surface phenotype of DCs include CDla+, CD4+, CD86+, or HLA-DR. The term DCs encompasses both immature and mature DCs. According to a specific embodiment the DCs comprise immature DCs. Specific cell surface phenotype of immature DCs may be lin−/CD11c+/CD83−.

The cells of the invention may be naïve or genetically modified depending on the application needed (e.g. on the disease to be treated). Such determinations are well within the ability of one of ordinary skill in the art.

According to one embodiment, there is provided genetically modified immune cells.

According to another embodiment, the immune cells express a chimeric antigen receptor (CAR) or a modified T cell receptor (TCR).

Accordingly, the immune cells (e.g. T cells, NK cells, dendritic cells) of the invention may be transduced to express a TCR or a CAR.

As used herein "transduction with a TCR" refers to cloning of two chains (i.e., polypeptide chains), such as, an alpha chain of a T cell receptor (TCR), a beta chain of a TCR, a gamma chain of a TCR, a delta chain of a TCR, or a combination thereof (e.g. $\alpha\beta$ chains or $\gamma\delta$ chains). According to one embodiment, the TCR comprises the variable region of a TCR (e.g. $\alpha$- and $\beta$-chains or $\gamma$- and $\delta$-chains). Method of transducing cells (e.g. T cells) with a TCR (e.g. to generated TCR-T cells) are known in the art and are disclosed e.g. in Nicholson et al. Adv Hematol. 2012; 2012:404081; Wang and Rivibre Cancer Gene Ther. 2015 March; 22(2):85-94); and Lamers et al., Cancer Gene Therapy (2002) 9, 613-623.

As used herein "transducing with a CAR" refers to cloning of a nucleic acid sequence encoding a chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. Method of transducing cells (e.g. T cells) with a CAR (e.g. to generate CAR-T) are known in the art and are disclosed e.g. in Davila et al. Oncoimmunology. 2012 Dec. 1; 1(9):1577-1583; Wang and Rivibre Cancer Gene Ther. 2015 March; 22(2):85-94); and Maus et al. Blood. 2014 Apr. 24; 123(17):2625-35.

According to one embodiment, the genetically modified immune cells are T cells. According to one embodiment, the genetically modified T cells express a transgenic TCR (TCR-T) or a CAR (CAR-T).

Thus, the cells (in suspension) of the invention (e.g. T cells) may be modified for therapy (e.g. anti-cancer or anti-viral adoptive cell therapy) by redirecting the cell specificity (e.g. T cell specificity) by promoting presentation of a receptor targeting a disease antigen (e.g. tumor or viral antigen) by way of transducing with a T cell receptor (TCR) or a chimeric antigen receptor (CAR).

According to some embodiments of the invention, the immune cells (e.g. T cells) expressing a TCR or a CAR are generated to target a diseases cell expressing a specific ligand (e.g. antigen) such as a cell of a tumor, viral or autoimmune disease. For example, TCR or CAR expressing immune cells may be generated to target malignant diseases e.g. follicular lymphoma (CD20 or GD2), neuroblastoma (CD171), non-Hodgkin lymphoma (CD20), lymphoma (CD19), glioblastoma (IL13R$\alpha$2), chronic lymphocytic leukemia or CLL and acute lymphocytic leukemia or ALL (both CD19); solid tumors including, but not limited to, ovarian, prostate, breast, renal, colon, neuroblastoma and others; and cells harboring viruses such as, but not limited to, HIV.

Depending on the application, the method may be effected using cells which are syngeneic or non-syngeneic with the subject.

As used herein, the term "syngeneic" cells refer to cells which are essentially genetically identical with the subject or essentially all lymphocytes of the subject. Examples of syngeneic cells include cells derived from the subject (also referred to in the art as an "autologous"), from a clone of the subject, or from an identical twin of the subject.

As used herein, the term "non-syngeneic" cells refer to cells which are not essentially genetically identical with the subject or essentially all lymphocytes of the subject, such as allogeneic cells or xenogeneic cells.

As used herein, the term "allogeneic" refers to cells which are derived from a donor who is of the same species as the subject, but which is substantially non-clonal with the subject. Typically, outbred, non-zygotic twin mammals of the same species are allogeneic with each other. It will be appreciated that an allogeneic cell may be HLA identical, partially HLA identical or HLA non-identical (i.e. displaying one or more disparate HLA determinant) with respect to the subject.

As used herein, the term "xenogeneic" refers to a cell which substantially expresses antigens of a different species relative to the species of a substantial proportion of the lymphocytes of the subject. Typically, outbred mammals of different species are xenogeneic with each other.

The present invention envisages that xenogeneic cells are derived from a variety of species. Thus, according to one embodiment, the cells may be derived from any mammal. Suitable species origins for the cells comprise the major domesticated or livestock animals and primates. Such animals include, but are not limited to, porcines (e.g. pig), bovines (e.g., cow), equines (e.g., horse), ovines (e.g., goat, sheep), felines (e.g., *Felis domestica*), canines (e.g., *Canis domestica*), rodents (e.g., mouse, rat, rabbit, guinea pig, gerbil, hamster), and primates (e.g., chimpanzee, rhesus monkey, macaque monkey, marmoset).

Cells of xenogeneic origin (e.g. porcine origin) are preferably obtained from a source which is known to be free of zoonoses, such as porcine endogenous retroviruses. Similarly, human-derived cells or tissues are preferably obtained from substantially pathogen-free sources.

According to an embodiment of the present invention, the subject is a human being and the cells are from a human origin.

According to one embodiment, the subject is a human being and the cells are from a xenogeneic origin (e.g. porcine origin).

According to one embodiment, the cells are non-syngeneic with the subject.

According to one embodiment, the cells are allogeneic with the subject.

According to one embodiment, the cells are xenogeneic with the subject.

According to one embodiment, the cells are syngeneic with the subject (e.g. autologous).

Depending on the application and available sources, the cells of the present invention may be obtained from a prenatal organism, postnatal organism, an adult or a cadaver donor. Such determinations are well within the ability of one of ordinary skill in the art.

Any method known in the art may be employed to obtain cells for transplantation. Thus, for example, immune cells (e.g. T cells, B cells, NK cells, DCs) may be obtained by collecting peripheral blood from a donor (e.g. from a Tcm cell donor as described in detail hereinbelow). Methods of collecting peripheral blood are well known in the art and include, but are not limited to, drawing of up to 500-1000 ml whole blood from a donor (e.g. Tcm cell donor as described in detail hereinbelow) and collection in a container containing an anti-coagulant (e.g. heparin or citrate) or by apheresis, a procedure in which the peripheral blood of an individual is passed through an apparatus, yielding a predominant constituent (e.g. mononuclear cells such as lymphocytes, monocytes or dendritic cells), and returning the other constituents to the subject's circulation. Alternatively, cells in suspension (i.e. non-hematopoietic cells or hematopoietic cells which are not stem cells) may be obtained by in-vitro or ex-vivo culture of cells. It will be appreciated that the cells in suspension (i.e. non-hematopoietic cells or hematopoietic cells which are not stem cells) of the invention may be of fresh or frozen (e.g., cryo-preserved) preparations, as discussed below.

According to another example, cells may be obtained from an organ or tissue.

According to one embodiment, the organ or tissue is from a fetal organism. The fetal organism may be of any of a human or xenogeneic origin (e.g. porcine) and at any stage of gestation. Such a determination is in the capacity of one of ordinary skill in the art.

According to one embodiment, the fetal organ or tissue comprises a fetal pulmonary tissue, a fetal pancreatic tissue, a fetal nephric tissue, a fetal hepatic tissue, a fetal cardiac tissue, a fetal brain tissue, a fetal spleen tissue, a fetal intestinal tissue, a fetal skin tissue, a fetal fallopian tube tissue, and a fetal ovarian tissue.

Various methods may be employed to obtain an organ or tissue from a fetal organism. Thus, for example, obtaining a tissue (e.g. liver, pancreas or lung tissue) may be effected by harvesting the tissue from a developing fetus, e.g. by a surgical procedure, at a stage of gestation corresponding to human 14-24 weeks of gestation. It will be understood by those of skill in the art that the gestational stage of an organism is the time period elapsed following fertilization of the oocyte generating the organism.

Likewise, various methods may be employed to obtain an organ or tissue from an adult organism (e.g. live or cadaver). Thus, for example, obtaining a tissue (e.g. liver, pancreas or lung tissue) may be effected by harvesting the tissue from an organ donor by a surgical procedure e.g. laparotomy or laparoscopy.

Alternatively, a tissue may be obtained by in-vitro or ex-vivo culture of cells, organs or tissues. Such controlled in-vitro differentiation of cells, tissues or organs is routinely performed, for example, using culturing of embryonic stem cell lines to generate cultures containing cells/tissues/organs of desired lineages.

According to one embodiment, the cells of the present invention are ex-vivo differentiated from adult stem cells or pluripotent stem cells, such as embryonic stem cells (ES cells) or iPS.

The phrase "embryonic stem cells" or "ES cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763), embryonic germ (EG) cells which are obtained from the genital tissue of a fetus any time during gestation, preferably before 10 weeks of gestation, and cells originating from an unfertilized ovum which are stimulated by parthenogenesis (parthenotes).

Embryonic stem cells (e.g., human ESCs) originating from an unfertilized ovum stimulated by parthenogenesis (parthenotes) are known in the art (e.g., Zhenyu Lu et al., 2010. J. Assist Reprod. Genet. 27:285-291; "Derivation and long-term culture of human parthenogenetic embryonic stem cells using human foreskin feeders", which is fully incorporated herein by reference). Parthenogenesis refers to the initiation of cell division by activation of ova in the absence of sperm cells, for example using electrical or chemical stimulation. The activated ovum (parthenote) is capable of developing into a primitive embryonic structure (called a blastocyst) but cannot develop to term as the cells are pluripotent, meaning that they cannot develop the necessary extra-embryonic tissues (such as amniotic fluid) needed for a viable human foetus.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation, which re-program the cell to acquire embryonic stem cells characteristics. According to some embodiments of the invention, the induced pluripotent stem cells are formed by inducing the expression of one or more of Oct-4, Sox2, Kfl4 and/or c-Myc in a somatic cell. According to one embodiment, all of Oct-4, Sox2, Kfl4 and c-Myc are induced in a somatic cell.

According to one embodiment, the pluripotent stem cells are not a result of embryo destruction.

The phrase "adult stem cells" (also called "tissue stem cells" or a stem cell from a somatic tissue) refers to any stem cell derived from a somatic tissue [of either a postnatal or prenatal animal (especially the human)]. The adult stem cell is generally thought to be a multipotent stem cell, capable of differentiation into multiple cell types. Adult stem cells can be derived from any adult, neonatal or fetal tissue such as adipose tissue, skin, kidney, liver, prostate, pancreas, intestine, bone marrow and placenta.

For example, for generation of pulmonary cells from embryonic stem cells by in vitro differentiation see Otto W R., 1997. Int J Exp Pathol. 78:291-310.

For example, for generation of cardiomyocytes from embryonic stem cells by in vitro differentiation see Paquin et al., Proc. Nat. Acad. Sci. (2002) 99:9550-9555.

For example, for generation of pancreatic cells from embryonic stem cells by in vitro differentiation see Shi et al. Stem Cells. 2005 May; 23(5):656-62.

For example, for in vitro differentiation of nephric cells from embryonic stem cells see Takasato et al. Nature Cell Biology 16, 118-126 (2014).

For example, for in vitro differentiation of hepatic cells from embryonic stem cells see Touboul et al., Hepatology. 2010 May; 51(5):1754-65.

Embryonic stem cells have also been induced to differentiate into neural or glial lineages [Reubinoff et al., Nature Biotechnology (2001) 19:1134-1140; U.S. Pat. No. 5,851, 832].

After organ/tissue is obtained, the present invention further contemplates generation of an isolated population of cells therefrom.

The differentiated cells may be comprised in a suspension of single cells or cell aggregates of no more than 5, 10, 50, 100, 200, 300, 400, 500, 1000, 1500, 2000 cells in an aggregate.

The cell suspension of the invention may be obtained by any mechanical or chemical (e.g. enzymatic) means. Several methods exist for dissociating cell clusters to form cell suspensions (e.g. single cell suspension) from primary tissues, attached cells in culture, and aggregates, e.g., physical forces (mechanical dissociation such as cell scraper, trituration through a narrow bore pipette, fine needle aspiration, vortex disaggregation and forced filtration through a fine nylon or stainless steel mesh), enzymes (enzymatic dissociation such as trypsin, collagenase, Accutase and the like) or a combination of both.

Thus, for example, enzymatic digestion of tissue/organ into isolate cells can be performed by subjecting the tissue to an enzyme such as type IV Collagenase (Worthington biochemical corporation, Lakewood, N.J., USA) and/or Dispase (Invitrogen Corporation products, Grand Island N.Y., USA). For example, the tissue may be enzyme digested by finely mincing tissue with a razor blade in the presence of e.g. collagenase, dispase and $CaCl_2$ at 37° C. for about 1 hour. The method may further comprise removal of nonspecific debris from the resultant cell suspension by, for example, sequential filtration through filters (e.g. 70- and 40-μm filters), essentially as described under "General Materials and Experimental Methods" of the Examples section which follows.

Furthermore, mechanical dissociation of tissue into isolated cells can be performed using a device designed to break the tissue to a predetermined size. Such a device can be obtained from CellArtis Goteborg, Sweden. Additionally or alternatively, mechanical dissociation can be manually performed using a needle such as a 27 g needle (BD Microlance, Drogheda, Ireland) while viewing the tissue/cells under an inverted microscope.

Following enzymatic or mechanical dissociation of the tissue, the dissociated cells are further broken to small clumps using 200 μl Gilson pipette tips (e.g., by pipetting up and down the cells).

According to the present invention, the cell suspension of differentiated cells comprises viable cells. Cell viability may be monitored using any method known in the art, as for example, using a cell viability assay (e.g. MultiTox Multiplex Assay available from Promega), Flow cytometry, Trypan blue, etc.

Typically, the differentiated cells are immediately used for transplantation. However, in situations in which the cells are to be maintained in suspension prior to transplantation, e.g. for 1-12 hours, the cells may be cultured in a culture medium which is capable of supporting their viability. Such a culture medium can be a water-based medium which includes a combination of substances such as salts, nutrients, minerals, vitamins, amino acids, nucleic acids, proteins such as cytokines, growth factors and hormones, all of which are needed for maintaining the isolated population of differentiated cells in an viable state. For example, a culture medium according to this aspect of the present invention can be a synthetic tissue culture medium such as RPMI-1640 (Life Technologies, Israel), Ko-DMEM (Gibco-Invitrogen Corporation products, Grand Island, N.Y., USA), DMEM/F12 (Biological Industries, Beit Haemek, Israel), Mab ADCB medium (HyClone, Utah, USA) or DMEM/F12 (Biological Industries, Beit Haemek, Israel) supplemented with the necessary additives. Preferably, all ingredients included in the culture medium of the present invention are substantially pure, with a tissue culture grade.

The differentiated cells may also be stored under appropriate conditions (typically by freezing) to keep the cells (e.g. differentiated cells) alive and functioning for use in transplantation. According to one embodiment, the differentiated cells are stored as cryopreserved populations. Other preservation methods are described in U.S. Pat. Nos. 5,656, 498, 5,004,681, 5,192,553, 5,955,257, and 6,461,645. Methods for banking stem cells are described, for example, in U.S. Patent Application Publication No. 2003/0215942.

The cells in suspension (i.e. non-hematopoietic cells or hematopoietic cells which are not stem cells) of the invention may comprise a heterogeneous or a homogenous population of cells. Thus, according to one embodiment, the cells comprise a pure population of CD8+ T cells or a pure population of genetically modified T cells (e.g. T cells transduced with a CAR or with a TCR, i.e. CAR-T or TCR-T, respectively, targeting a specific antigen). According to another embodiment, the cells comprise a mixed population of cells (at least two types of cells), such as but not limited to, T cells e.g. CD8+ T cells and CD4+ T cells, or a mixed population of T cells and B cells. Such determinations are well within the capacity of one of skill in the art. Alternatively, the cells may comprise cells obtained from more than one cell donor.

As illustrated in the Examples section which follows, anti-third party central memory T cells are endowed with specific veto activity and can be used as graft facilitating cells in situations in which non-syngeneic (e.g. allogeneic) cell transplantation is warranted.

Thus, according to one embodiment, in order to avoid graft rejection (i.e. of the cells in suspension i.e. non-hematopoietic cells or hematopoietic cells which are not stem cells), to provide an anti-disease activity (at least in the case when the cells are syngeneic with the subject) and/or avoid graft versus host disease (i.e. by the cells in suspension i.e. non-hematopoietic cells or hematopoietic cells which are not stem cells) the subject is administered anti-third party cells having a central memory T-lymphocyte (Tcm) phenotype, the cells being tolerance-inducing cells and capable of homing to the lymph nodes following transplantation.

The phrase "anti-third party cells" as used herein refers to T lymphocytes which are directed (by T cell recognition) against a third party antigen or antigens.

As used herein the phrase "third party antigen or antigens" refers to a soluble or non-soluble (such as membrane associated) antigen or antigens which are not present in either the donor or recipient, as depicted in detail infra.

For example, third party antigens can be third party cells, cell antigens (e.g. cell surface antigens), antigens associated with a malignant disease (e.g. tumor antigens), antigens of viruses (i.e. viral antigen), such as for example, Epstein-Barr virus (EBV) or cytomegalovirus (CMV), or antigens of bacteria (i.e. bacterial antigen), such as flagellin. Viral or bacterial antigens can be presented by cells (e.g., cell line) infected therewith or otherwise made to express viral/bacterial proteins.

Autologous or non-autologous antigen presenting cells, or artificial vehicle or artificial antigen presenting cells, can be used to present short synthetic peptides fused or loaded thereto or to present protein extracts or purified proteins. Such short peptides, protein extracts or purified proteins may be viral or bacterial derived peptides or peptides representing any other antigen.

Dedicated software can be used to analyze viral or other sequences to identify immunogenic short peptides, i.e., peptides presentable in context of class I MHC or class II MHC.

Third party cells can be either allogeneic or xenogeneic with respects to the recipient (explained in further detail hereinbelow). In the case of allogeneic third party cells, such cells have HLA antigens different from that of the donor but which are not cross reactive with the recipient HLA antigens, such that anti-third party cells generated against such cells are not reactive against a transplant or recipient antigens.

According to an embodiment of the present invention the allogeneic or xenogeneic third party cells are stimulatory cells selected from the group consisting of cells purified from peripheral blood lymphocytes (PBL), spleen or lymph nodes, cytokine-mobilized PBLs, in vitro expanded antigen-presenting cells (APC), in vitro expanded dendritic cells (DC) and artificial antigen presenting cells.

The artificial APC of the present invention may be engineered to exhibit autologous MHC with a $3^{rd}$ party peptide or a $3^{rd}$ party MHC without being pulsed with an exogenous peptide. Thus, according to one embodiment, the artificial APC comprises K562 tumor cells transfected with a third party MHC determinant and a co-stimulatory molecule [as previously described e.g. Suhoski M M et al., Mol Ther. (2007) 15(5): 981-8], or fibroblasts transfected with same.

Third party antigens can be presented on the cellular, viral or bacterial surfaces or derived and/or purified therefrom. Additionally, a viral or bacterial antigen can be displayed on an infected cell and a cellular antigen can be displayed on an artificial vehicle such as a liposome or an artificial antigen presenting cell (e.g. leukemic or fibroblast cell line transfected with the third party antigen or antigens).

The third party antigen may further comprise a synthetic peptide presented by autologous presenting cells, non-autologous presenting cells or on an artificial vehicle or on artificial antigen presenting cells.

In addition, third party antigens can, for example, be proteins extracted or purified from a variety of sources. An example of a purified protein which can serve as a third party antigen according to the present invention is ovalbumin. Other examples are envisaged.

Utilizing cells, virally infected cells, bacteria infected cells, viral peptides presenting cells or bacteria peptides presenting cells as third party antigens is particularly advantageous since such third party antigens include a diverse array of antigenic determinants and as such direct the formation of anti-third party cells of a diverse population, which may further serve in faster reconstitution of T-cells in cases where such reconstitution is required, e.g., following lethal or sublethal irradiation or chemotherapy procedure.

Furthermore, when anti-third party cells are directed against third party antigens, the cells are endowed with anti-disease activity. The term "anti-disease activity" refers to the activity (e.g. killing capability) of the Tcm cells against a diseased cell (e.g. cancer cell, such as graft versus leukemia, GVL, activity). This activity is typically due to TCR independent killing mediated by LFA1-I/CAM1 binding [Arditti et al., Blood (2005) 105(8):3365-71. Epub 2004 Jul. 6].

According to one embodiment, the third party cells comprise dendritic cells.

According to one embodiment, the third party cells comprise mature dendritic cells.

Methods of generating third party dendritic cells, which may be used as stimulatory cells for inducing Tcm cells, are well known in the art. Thus, as a non-limiting example, peripheral blood mononuclear cells (PBMCs) may be obtained from a third party non-syngeneic cell donor [e.g. in case the Tcm cells are syngeneic, e.g. autologous, the dendritic cells (DCs) may be non-syngeneic, e.g. allogeneic, with respect to the subject; whereas if the Tcm cells are non-syngeneic, e.g. allogeneic, the DCs are selected from a donor being non-syngeneic, e.g. allogeneic, and HLA mismatched with both the subject and the Tcm cells]. Monocytes may then be isolated by plastic adherence and cultured (e.g. in cell culture plates) using DC cell medium (e.g. Cellgro DC medium) supplemented with human serum (e.g. 1% human serum), penicillin/streptomycin and GM-CSF (e.g. 800 IU/ml) and IL-4 (e.g. 20 ng/ml) (available from e.g. Peprotech, Hamburg, Germany). After about 24-72 h (e.g. 48 h) of culture, DC medium may be added comprising GM-CSF (e.g. 1600 IU/ml) and IL-4 (e.g. 20 ng/ml). About 12-36 h (e.g. 24 h) later, non-adherent cells may be harvested, and large cells (mostly immature DC) may be resuspended in fresh medium containing GM-CSF (e.g. 800 IU/ml), IL-4 (e.g. 20 ng/ml), LPS (e.g. from *E. coli* 055:B5 at e.g. 10 ng/ml) and IFNγ (e.g. 100 IU/ml) (available from e.g. Peprotech, Hamburg, Germany), plated and incubated overnight. The next day, non-adherent cells may be discarded, and adherent DCs may be gently removed using e.g. cold PBS/1% HS after incubation on ice for about 15-30 minutes (e.g. 20 minutes), thereby obtaining large cells consisting of mature DC.

According to one embodiment, the third party cells comprise irradiated dendritic cells.

Thus, according to one embodiment, the DCs are irradiated with about 5-10 Gy, about 10-20 Gy, about 20-30 Gy, about 20-40 Gy, about 20-50 Gy, about 10-50 Gy. According to a specific embodiment, the DCs are irradiated with about 10-50 Gy (e.g. 30 Gy).

According to some embodiments, the anti-third party cells of the present invention comprise a central memory T-lymphocyte (Tcm) phenotype.

The phrase "central memory T-lymphocyte (Tcm) phenotype" as used herein refers to a subset of T cytotoxic cells which home to the lymph nodes. Cells having the Tcm phenotype, in humans, typically comprise a CD3+/CD8+/CD62L+/CD45RO+/CD45RA− signature. It will be appreciated that Tcm cells may express all of the signature markers on a single cell or may express only part of the signature markers on a single cell.

It will be appreciated that at least 30%, at least 40%, at least 50%, at least 55%, at least 60%, at least 65%, at least 70%, at least 75%, at least 80%, at least 85%, at least 90%, at least 95% or even 100% of the anti-third party cells are CD3+CD8+ cells. According to a specific embodiment, the anti-third party cells comprise about 70-90% CD3+CD8+ cells.

It will be appreciated that at least 30%, at least 40%, at least 50%, at least 55%, at least 60%, at least 65%, at least 70%, at least 75%, at least 80%, at least 85%, at least 90%, at least 95% or even 100% of the CD3+CD8+ cells have the Tcm cell signature. According to a specific embodiment, about 30-80% of the CD3+CD8+ cells have the Tcm cell signature (e.g. 40-50%).

According to one embodiment, at least 50% of the isolated population of cells are CD3+CD8+ cells of which at least 50% have the signature.

As mentioned, the Tcm cells typically home to the lymph nodes following transplantation. According to some embodiments, the anti-third party Tcm cells of the present invention may home to any of the lymph nodes following transplantation, as for example, the peripheral lymph nodes and mesenteric lymph nodes. The homing nature of these cells allows them to exert their tolerance effect in a rapid and efficient manner.

Thus, the anti-third party Tcm cells of the present invention are tolerance-inducing cells.

The phrase "tolerance inducing cells" as used herein refers to cells which provoke decreased responsiveness of the recipient's cells (e.g. recipient's T cells) when they come in contact with the recipient's cells as compared to the responsiveness of the recipient's cells in the absence of administered tolerance inducing cells. Tolerance inducing cells include veto cells (i.e. T cells which lead to apoptosis of host T cells upon contact with same) as was previously described in PCT Publication Nos. WO 2001/049243 and WO 2002/102971.

The term "veto activity" relates to immune cells (e.g. donor derived cells) which lead to inactivation of anti-donor recipient T cells upon recognition and binding to the veto cells. According to one embodiment, the inactivation results in apoptosis of the anti-donor recipient T cells.

The Tcm cells of the invention are also non-GVHD inducing cells.

The term "non-GVHD" as used herein refers to having substantially reduced or no graft versus host inducing reactivity. Thus, the cells of the present invention are generated as to not significantly cause graft versus host disease (GVHD) as evidenced by survival, weight and overall appearance of the transplanted subject 30-100 days.

According to one embodiment, the cells of the present invention have at least 20%, at least 30%, at least 40%, at least 50%, at least 55%, at least 60%, at least 65%, at least 70%, at least 75%, at least 80%, at least 85%, at least 90%, at least 95% or even 100% reduced reactivity against a host relative to transplantation of T cells which are not anti-third party Tcm cells.

Thus, the anti-third party Tcm cells of the present invention may be used as adjuvant therapy for transplantation of cells in suspension, i.e. non-hematopoietic cells or hematopoietic cells which are not stem cells (as described hereinabove). In addition the Tcm cells of the present invention are also endowed with anti-disease activity (e.g. anti-tumor cell activity) and thus may be used for disease treatment (or as part of the disease treatment).

According to some embodiments, the Tcm cells of the present invention may be non-genetically modified cells or genetically modified cells (e.g. cells which have been genetically engineered to express or not express specific genes, markers or peptides or to secrete or not secrete specific cytokines). Any method known in the art may be implemented in genetically engineering the cells, such as by inactivation of the relevant gene/s or by insertion of an antisense RNA interfering with polypeptide expression (see e.g. WO/2000/039294, which is hereby incorporated by reference).

Any method of producing anti-third party Tcm cells can be used in accordance with the present invention as was previously described in PCT Publication Nos. WO 2010/049935, WO 2012/032526 and WO 2013/035099, incorporated herein by reference.

Thus, for example, anti-third party cells having the Tcm phenotype may be generated by a method comprising: (a) contacting peripheral blood mononuclear cells (PBMCs) with a third party antigen or antigens in the presence or absence of IL-21 so as to allow enrichment of antigen reactive cells; and (b) culturing the cells resulting from step (a) in the presence of IL-21, IL-15 and IL-7 so as to allow proliferation of cells comprising the central memory T-lymphocyte (Tcm) phenotype.

According to one embodiment, the PBMCs in step (a) are contacted with a third party antigen or antigens in the absence of IL-21.

According to one embodiment, the PBMCs in step (a) are contacted with a third party antigen or antigens in the presence of IL-21.

According to one embodiment, the cells resulting from step (a) are cultured in an antigen free environment (e.g. without the addition of an antigen to the cell culture) in the presence of only IL-15, IL-21 and/or IL-7 may optionally be added.

The anti-third party Tcm cells of the present invention are typically generated by first contacting syngeneic (e.g. autologous) or non-syngeneic (e.g. non-autologous such as allogeneic or xenogeneic) peripheral blood mononuclear cells (PBMCs) with a third party antigen or antigens (such as described above) in a culture supplemented with IL-21 (e.g. in an otherwise cytokine-free culture i.e., without the addition of any additional cytokines). This step is typically carried out for about 12-24 hours, about 12-36 hours, about 12-72 hours, 24-48 hours, 24-36 hours, about 24-72 hours, about 48-72 hours, 1-2 days, 2-3 days, 1-3 days, 2-4 days, 1-5 days, 2-5 days, 2-6 days, 1-7 days, 5-7 days, 2-8 days, 8-10 days or 1-10 days and allows enrichment of antigen reactive cells.

According to a specific embodiment, contacting of syngeneic or non-syngeneic PBMCs with a third party antigen or antigens (such as described above) in a culture supplemented with IL-21 (otherwise cytokine-free culture) is effected for 1-5 days (e.g. 3 days).

This step is typically carried out in the presence of about 0.001-3000 IU/ml, 0.01-3000 IU/ml, 0.1-3000 IU/ml, 1-3000 IU/ml, 10-3000 IU/ml, 100-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 100-1000 IU/ml, 250-1000 IU/ml, 500-1000 IU/ml, 750-1000 IU/ml, 10-500 IU/ml, 50-500 IU/ml, 100-500 IU/ml, 250-500 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-21.

According to a specific embodiment, the concentration of IL-21 is 50-150 IU/ml (e.g. 100 IU/ml).

According to a specific embodiment, contacting the syngeneic or non-syngeneic PBMCs with a third party antigen or antigens is effected in a cytokine-free culture (e.g. supplemented with only IL-21), such a culture condition enables survival and enrichment of only those cells which undergo stimulation and activation by the third party antigen or antigens (i.e. of antigen reactive cells) as these cells secrete cytokines (e.g. IL-2) which enable their survival (all the rest of the cells die under these culture conditions).

The ratio of third party antigen or antigens (e.g. dendritic cell) to PBMCs is typically about 1:2 to about 1:10 such as about 1:4, about 1:6, about 1:8 or about 1:10. According to a specific embodiment, the ratio of third party antigen or antigens (e.g. dendritic cell) to PBMCs is about 1:2 to about 1:8 (e.g. 1:5).

Next, the anti-third party cells are cultured in the presence of IL-21, IL-15 and/or IL-7 (e.g. in an antigen free environment) so as to allow proliferation of cells comprising the Tcm phenotype. This step is typically carried out for about 12-24 hours, about 12-36 hours, about 12-72 hours, 24-48 hours, 24-36 hours, about 24-72 hours, about 48-72 hours, 1-20 days, 1-15 days, 1-10 days, 1-5 days, 5-20 days, 5-15 days, 5-10 days, 1-2 days, 2-3 days, 1-3 days, 2-4 days, 2-5 days, 2-8 days, 2-10 days, 4-10 days, 4-8 days, 6-8 days, 8-10 days, 7-9 days, 7-11 days, 7-13 days, 7-15 days, 10-12 days, 10-14 days, 12-14 days, 14-16 days, 14-18 days, 16-18 days or 18-20 days. According to a specific embodiment, the anti-third party cells are cultured in the presence of IL-21, IL-15 and IL-7 in an antigen free environment (e.g. without the addition of an antigen) for about 7-11 days (e.g. 8 days).

This step is typically carried out in the presence of IL-21 at a concentration of about 0.001-3000 IU/ml, 0.01-3000 IU/ml, 0.1-3000 IU/ml, 1-3000 IU/ml, 10-3000 IU/ml, 100-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 100-1000 IU/ml, 250-1000 IU/ml, 500-1000 IU/ml, 750-1000 IU/ml, 10-500 IU/ml, 50-500 IU/ml, 100-500 IU/ml, 250-500 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-21. According to a specific embodiment, the concentration of IL-21 is 50-150 IU/ml (e.g. 100 IU/ml).

This step is further carried out in the presence of IL-15 at a concentration of about This step is further carried out in the presence of IL-15 at a concentration of about 0.001-3000 IU/ml, 0.01-3000 IU/ml, 0.1-3000 IU/ml, 1-3000 IU/ml, 10-3000 IU/ml, 100-3000 IU/ml, 125-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 100-1000 IU/ml, 125-1000 IU/ml, 250-1000 IU/ml, 500-1000 IU/ml, 750-1000 IU/ml, 10-500 IU/ml, 50-500 IU/ml, 100-500 IU/ml, 125-500 IU/ml, 250-500 IU/ml, 250-500 IU/ml, 125-250 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-15. According to a specific embodiment the concentration of IL-15 is 100-150 IU/ml (e.g. 125 IU/ml).

This step is further carried out in the presence of IL-7 at a concentration of about 0.001-3000 IU/ml, 0.01-3000 IU/ml, 0.1-3000 IU/ml, 1-3000 IU/ml, 10-3000 IU/ml, 30-3000 IU/ml, 100-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 30-1000 IU/ml, 100-1000 IU/ml, 250-1000 IU/ml, 500-1000 IU/ml, 750-1000 IU/ml, 10-500 IU/ml, 30-500 IU/ml, 50-500 IU/ml, 100-500 IU/ml, 250-500 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-7. According to a specific embodiment the concentration of IL-7 is 10-50 IU/ml (e.g. 30 IU/ml).

The present inventors have collected through laborious experimentation and screening a number of criteria which may be harnessed towards to improving the proliferation of anti-third party cells comprising a central memory T-lymphocyte (Tcm) phenotype being devoid of graft versus host (GVH) reactive cells and/or being enhanced for anti-disease (e.g. GVL) reactive cells.

According to one embodiment, the PBMCs are depleted of adherent cells prior to contacting with a third party antigen or antigens in the presence of IL-21.

According to one embodiment, the PBMCs are depleted of CD4+ and/or CD56+ cells prior to contacting with a third party antigen or antigens in the presence of IL-21.

According to one embodiment, the PBMCs are selected for CD45RA+ cells prior to contacting with a third party antigen or antigens in the presence of IL-21.

Depletion of CD4$^+$ and/or CD56+ cells may be carried out using any method known in the art, such as by affinity based purification (e.g. such as by the use of MACS beads, FACS sorter and/or capture ELISA labeling). Such a step may be beneficial in order to increase the purity of the CD8$^+$ cells within the culture (i.e. eliminate other lymphocytes within the cell culture e.g. T CD4$^+$ cells or NK cells) or in order to increase the number of CD8$^+$ T cells.

According to one embodiment, the PBMCs comprise non-adherent cells.

According to one embodiment, the PBMCs comprise CD8+ T cells.

According to one embodiment, the PBMCs comprise naïve CD8+ T cells.

Selection of naïve CD8+ T cells may be effected by selection of cells expressing CD45RA+ and/or cells expressing CD45RO– and may be carried out using any method known in the art, such as by affinity based purification (e.g. such as by the use of MACS beads, FACS sorter and/or capture ELISA labeling).

According to one embodiment, the PBMCs comprise CD45RA+ cells.

An additional step which may be carried out in accordance with the present teachings include culturing the PBMCs cells with a third party antigen or antigens in the presence of IL-21, IL-15 and IL-7 prior to removing the third party antigen or antigens from the cell culture (i.e. prior to generating an antigen free environment). This step is typically carried out for about 12-24 hours, about 12-36 hours, about 12-72 hours, 24-48 hours, 24-36 hours, about 24-72 hours, about 48-72 hours, 1-2 days, 2-3 days, 1-3 days, 2-4 days, 1-5 days or 2-5 days, and is effected at the same doses of IL-21, IL-15 and IL-7 indicated above. According to a specific embodiment, culturing the PBMCs cells with a third party antigen or antigens in the presence of IL-21, IL-15 and IL-7 is carried out for 12 hours to 4 days (e.g. 1-2 days).

Additionally or alternatively, an additional two step process which allows selection and isolation of activated cells may be carried out. Such a selection step aids in removal of potential host reactive T cells (e.g. alloreactive cells) in situations where the PBMCs are non-syngeneic with respect to the subject (as described in further detail below).

Thus, isolating activated cells may be carried out in a two stage approach. In the first stage activated cells are selected before culturing the cells in the presence of IL-15 and IL-7. This first stage is typically carried out after the initial contacting of the PBMCs with a third party antigen or antigens in the presence of IL-21. This selection process picks only those cells which were activated by the third party antigen (e.g. express activation markers as described below) and is typically affected about 12-24 hours, about 24-36 hours, about 12-36 hours, about 36-48 hours, about 12-48 hours, about 48-60 hours, about 12-60 hours, about 60-72 hours, about 12-72 hours, about 72-84 hours, about 12-84 hours, about 84-96 hours, about 12-96 hours, after the initial contacting of the PBMCs with a third party antigen or antigens. According to a specific embodiment, the selection process is effected about 12-24 hours (e.g. 14 hours) after the initial contacting of the PBMCs with a third party antigen or antigens.

Isolating activated cells may be effected by affinity based purification (e.g. such as by the use of MACS beads, FACS sorter and/or capture ELISA labeling) and may be effected towards any activation markers including cell surface markers such as, but not limited to, CD69, CD44, CD25, CFSE, CD137 or non-cell surface markers such as, but not limited to, IFN-γ and IL-2. Isolating activated cells may also be effected by morphology based purification (e.g. isolating large cells) using any method known in the art (e.g. by FACS). Typically, the activated cells are also selected for expression of CD8$^+$ cells. Furthermore, any combination of the above methods may be utilized to efficiently isolate activated cells.

According to an embodiment of the present invention, selecting for activated cells is effected by selection of CD137+ and/or CD25+ cells.

The second stage of isolation of activated cells is typically carried out at the end of culturing (i.e. after culturing with IL-21, IL-15 and IL-7 without the addition of an antigen). This stage depletes alloreactive cells by depletion of those cells which were activated following contacting of the central memory T-lymphocyte (Tcm) with irradiated host antigen presenting cells (APCs e.g. dendritic cells). As mentioned above, isolating activated cells may be effected by affinity based purification (e.g. such as by the use of MACS beads, FACS sorter and/or capture ELISA labeling) and may be effected towards any activation markers including cell surface markers such as, but not limited to, CD69, CD44, CD25, CFSE, CD137 or non-cell surface markers such as, but not limited to, IFN-γ and IL-2.

According to an embodiment of the present invention, depleting the alloreactive cells is effected by depletion of CD137+ and/or CD25+ cells and/or IFNγ-capture.

Following are a number of non-limiting examples of protocols which can be used according to some embodiments of the invention.

According to one embodiment of the invention, there is provided a method of generating an isolated population of cells comprising anti-third party cells having a central memory T-lymphocyte (Tcm) phenotype, the cells being tolerance-inducing cells and capable of homing to the lymph nodes following transplantation, the method comprising: (a) treating non-adherent peripheral blood mononuclear cells (PBMCs) with an agent capable of depleting CD4+ and/or CD56+ cells so as to obtain CD8+ T cells; (b) contacting the CD8+ T cells with third party dendritic cells in the presence of IL-21 for 12 hours to 5 days so as to allow enrichment of antigen reactive cells; (c) culturing the cells resulting from step (b) with the third party dendritic cells in the presence of IL-21, IL-15 and IL-7 for 12 hours to 3 days; and (d) culturing the cells resulting from step (c) in the presence of IL-21, IL-15 and IL-7 in an antigen free environment (e.g. without the addition of an antigen) for 5-20 days so as to allow proliferation of cells comprising the central memory T-lymphocyte (Tcm) phenotype.

Thus, the anti-third party cells having a central memory T-lymphocyte (Tcm) phenotype of the invention are not naturally occurring and are not a product of nature. These cells are typically produced by ex-vivo manipulation (i.e. exposure to a third party antigen or antigens in the presence of specific cytokines).

The method of the present invention may be applied to treat any disease or condition in which transplantation of cells in suspension (i.e. non-hematopoietic cells or hematopoietic cells which are not stem cells) may be advantageous. Thus, the anti-third party Tcm cells of the invention can be used to facilitate transplantation of cells in suspension (i.e. non-hematopoietic cells or hematopoietic cells which are not stem cells) without the harmful effects of graft rejection and/or GVHD. For example, genetically modified immune cells, e.g. allogeneic T cells or NK cells engineered to express a chimeric antigen receptor (CAR) can be used to eradicate tumor cells, virally infected cells or cells presenting auto-antigens (e.g. in autoimmune diseases). Additionally allogeneic cells such as, liver, pancreas, spleen, kidney, heart, lung, skin, intestine, ovarian, fallopian tubes or brain cells can be transplanted to repopulate an injured or damaged organ. The tolerizing effect of the anti-third party Tcm cells of the invention enables their use in immune compromised individuals as well as in cases of non-malignant diseases, e.g. hematological diseases (e.g. anemia, thalassemia, and autoimmune diseases).

Thus, according to one aspect of the present invention there is provided a method of transplantation, the method comprising administering to a subject in need of transplantation of cells in suspension (i.e. non-hematopoietic cells or hematopoietic cells which are not stem cells), a therapeutically effective amount of anti-third party cells having a central memory T-lymphocyte (Tcm) phenotype, the cells being tolerance-inducing cells and capable of homing to the lymph nodes following transplantation.

According to one aspect of the present invention there is provided a therapeutically effective amount of anti-third party cells having a central memory T-lymphocyte (Tcm) phenotype, the anti-third party cells being tolerance-inducing cells and capable of homing to the lymph nodes following transplantation, for use in treating a subject in need of transplantation of cells in suspension, wherein the cells in suspension comprise non-hematopoietic cells or hematopoietic cells which are not stem cells.

As used herein, the term "subject" or "subject in need" refers to a mammal, preferably a human being, male or female at any age that is in need of a cell transplantation (i.e. transplantation of cells) or suffers from a disease which may be treated with a cell transplantation (i.e. transplantation of cells). Typically the subject is in need of transplantation (also referred to herein as recipient) due to a disorder or a pathological or undesired condition, state, or syndrome, or a physical, morphological or physiological abnormality which is amenable to treatment via cell transplantation. Examples of such disorders are provided further below.

As used herein, the phrase "transplantation" refers to administration of a bodily cell, e.g. a single cell or a group of cells, into a subject.

According to one embodiment, the method further comprises administering cells in suspension to the subject (i.e. non-hematopoietic cells or hematopoietic cells which are not stem cells).

According to another aspect there is provided a method of treating a disease in a subject in need thereof, the method comprising: (a) administering to the subject a therapeutically effective amount of cells in suspension, wherein the cells comprise non-hematopoietic cells or hematopoietic cells which are not stem cells; and (b) administering to the subject a therapeutically effective amount of anti-third party cells having a central memory T-lymphocyte (Tcm) phenotype, the cells being tolerance-inducing cells and capable of homing to the lymph nodes following transplantation.

According to another aspect there is provided a therapeutically effective amount of cells in suspension, wherein the cells in suspension comprise non-hematopoietic cells or hematopoietic cells which are not stem cells, and a therapeutically effective amount of anti-third party cells having a central memory T-lymphocyte (Tcm) phenotype, the anti-third party cells being tolerance-inducing cells and capable of homing to the lymph nodes following transplantation, for use in treating a disease in a subject in need thereof.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "a therapeutically effective amount" means an amount of active ingredients (i.e. cells in suspension and/or anti-third party Tcm cells) effective to prevent, alleviate or ameliorate symptoms of a disorder (e.g., malignant or non-malignant disease) or prolong the survival of the subject being treated.

Determination of the therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

For example, in case of cell transplantation the number of anti-third party Tcm cells infused to a recipient should be more than $1\times10^4$/Kg body weight. The number of anti-third party Tcm cells infused to a recipient should typically be in the range of $1\times10^3$/Kg body weight to $1\times10^4$/Kg body weight, range of $1\times10^4$/Kg body weight to $1\times10^5$/Kg body weight, range of $1\times10^4$/Kg body weight to $1\times10^6$/Kg body weight, range of $1\times10^4$/Kg body weight to $1\times10^7$/Kg body weight, range of $1\times10^4$/Kg body weight to $1\times10^8$/Kg body weight, range of $1\times10^3$/Kg body weight to $1\times10^5$/Kg body weight, range of $1\times10^4$/Kg body weight to $1\times10^6$/Kg body weight, range of $1\times10^6$/Kg body weight to $1\times10^7$/Kg body weight, range of $1\times10^5$/Kg body weight to $1\times10^7$/Kg body weight, range of $1\times10^6$/Kg body weight to $1\times10^8$/Kg body weight, or range of $1\times10^6$/Kg body weight to $1\times10^9$/Kg body weight. According to a specific embodiment, the number of anti-third party Tcm cells infused to a recipient should be in the range of $1\times10^6$/Kg body weight to $1\times10^8$/Kg body weight.

According to one embodiment, the disease is a malignant disease, a disease associated with transplantation of a graft, an infectious disease (e.g. viral infection, bacterial infection, fungal infection, protozoan infection or parasitic infections), an allergy, an inflammatory disease and/or an autoimmune disease.

Cancerous Diseases

Malignant diseases (also termed cancers) which can be treated by the method of some embodiments of the invention can be any solid or non-solid tumor and/or tumor metastasis.

Examples of cancer include, but are not limited to, carcinoma, lymphoma, blastoma, sarcoma, and leukemia. More particular examples of such cancers include squamous cell cancer, soft-tissue sarcoma, Kaposi's sarcoma, melanoma, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, rectal cancer, endometrial or uterine carcinoma, carcinoid carcinoma, salivary gland carcinoma, kidney or renal cancer, liver cancer, prostate cancer, vulval cancer, thyroid cancer, hepatic carcinoma, mesothelioma, multiple myeloma, post-transplant lymphoproliferative disorder (PTLD), and various types of head and neck cancer (e.g. brain tumor). The cancerous conditions amenable for treatment of the invention include metastatic cancers.

According to one embodiment, the malignant disease is a hematological malignancy. Exemplary hematological malignancies include, but are not limited to, leukemia [e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia, T-cell acute lymphocytic leukemia (T-ALL) and B-cell chronic lymphocytic leukemia (B-CLL)] and lymphoma [e.g., Hodgkin's disease, non-Hodgkin's lymphoma, Burkitt, cutaneous T cell, histiocytic, lymphoblastic, T cell, thymic, B cell, including low grade/follicular; small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia].

According to a specific embodiment, the malignant disease is a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer or a pancreatic cancer.

Inflammatory Diseases—

Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan OT. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydenham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth GS. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra HS. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov DG. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi AP. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth GS. Ann. Rev. Immunol. 8:647; Zimmet P. Diabetes Res Clin Pract 1996 October; 34 Suppl:S 125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra HS. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydenham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan OT. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection and rabies.

Graft Rejection Diseases

According to other embodiment, the disease is associated with transplantation of a graft. Examples of diseases associated with transplantation of a graft include, but are not limited to, graft rejection, chronic graft rejection, subacute graft rejection, hyperacute graft rejection, acute graft rejection, allograft rejection, xenograft rejection and graft-versus-host disease (GVHD).

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to a specific embodiment, the disease is a non-malignant disease.

According to another specific embodiment, the non-malignant disease is an organ dysfunction or failure, a cerebral ischemia, a Parkinson's disease, an Alzheimer's disease, a multiple sclerosis, a retinal disease, a diabetes mellitus (e.g. diabetes type I or diabetes type II) or a myogenic disease.

The multipotent character of MSCs, epithelial progenitor cells and EPCs makes these cells an attractive therapeutic tool and candidate for transplantation, capable of playing a role in a wide range of clinical or cosmetic applications.

Thus, the method of the invention may be used to treat a subject suffering from any medical condition who may benefit from transplantation of mesenchymal stem cells, epithelial progenitor cells and/or endothelial progenitor cells.

According to one embodiment, the medical condition may comprise a non-malignant disease, an autoimmune disease (also referred to as autoimmunity), a cosmetic treatment, replacing a tissue or an organ, or inducing or accelerating tissue repair or regeneration in a subject.

Tissues are not limited as long as they are tissues into which stromal cells can differentiate. Examples include all types of tissues in the living body, such as skin tissue, bone tissue, cartilage tissue, muscle tissue, adipose tissue, cardiac muscle tissue, neurological tissue, pulmonary tissue, gastrointestinal tissues, hepatic/biliary/pancreatic tissues, and genitourinary organs.

Examples of tissue in need of regeneration include, but are not limited to, tissues damaged by various pathological conditions due to ischemic/hypoperfusive/hypoxic conditions, trauma, burns, inflammation, autoimmunity, gene abnormalities, and the like.

Examples of the tissue other than a tissue in need of regeneration include blood tissues, muscle tissues, subcutaneous tissues, intradermal tissues, abdominal cavity, neural tissues and such.

Thus, mesenchymal stem cells or endothelial progenitor cells may be used to aid in tissue re-generation, to promote wound healing and to correct for a myriad of other inherited and acquired disorders. MSCs or EPCs may also be used in therapy of inflammatory conditions due to their ability to differentiate, provide trophic support, and modulate the innate immune response. The therapeutic potential of MSC or EPCs is being tested in multiple clinical trials for indications such as bone and cartilage repair, cardiac regeneration, critical limb ischemia, acute ischemic conditions, diabetes, Crohn's disease, cancer and GVHD.

Exemplary non-malignant diseases in which MSCs or EPCs may be used, include but are not limited to, organ dysfunction or failure, a cerebral ischemia, a Parkinson's disease, an Alzheimer's disease, a multiple sclerosis, a retinal disease, a diabetes mellitus and a myogenic disease.

According to one embodiment, MSCs or EPCs may be used to treat a bone disease, a bone damage, a cardiovascular disease, a cardiovascular injury, an ischemic disease and an ischemic injury.

Thus, the cells of the invention may be used to treat any tissue injured by ischemia or at risk of ischemic injury such as, but not limited to, skeletal muscle, cardiac muscle, kidney, liver, gut, brain, lung, vascular, dermal tissue, scalp, or eye.

According to one embodiment, MSCs or EPCs may be used to treat diseased or damaged bone in a subject (e.g. fractured bone). Diseased bone to be treated can include, but are not limited to, osteopenic bone, osteoporotic bone, necrotic bone, or ischemic bone.

Thus, MSCs or EPCs according to the present teachings can be used to treat neurodegenerative disorders, including but not limited to, familial and sporadic amyotrophic lateral sclerosis (FALS and ALS, respectively), Parkinson's disease, Huntington's disease, Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy), traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor), and Wernicke-Korsakoffs related dementia; and neurodegenerative diseases affecting sensory neurons include Friedreich's ataxia, diabetes, peripheral neuropathy, and retinal neuronal degeneration.

Exemplary autoimmune diseases in which MSCs or EPCs may be used for therapy are discussed in detail hereinabove. For example, MSCs or EPCs may be used for the treatment of multiple sclerosis; rheumatoid arthritis; systemic lupus erythematosus, scleroderma psoriasis; myasthenia gravis; Grave's disease, Crohn's disease; and ulcerative colitis.

According to one embodiment, when the progenitor cells are mesenchymal stem cells the disease is a medical condition comprising a cosmetic condition, a tissue or organ damage, an orthopedic condition, a neural condition, a heart disease or condition, a diabetes, a deafness, a Crohn's disease, an autoimmune disorder, a leukemia, a cancer, a sickle cell disease, an amyotrophic lateral sclerosis or a metabolic disorders.

According to one embodiment, when the progenitor cells are endothelial progenitor cells the disease is a medical condition comprising a bone disease, a bone damage, a cardiovascular disease, a cardiovascular injury, an ischemic disease, an ischemic injury, a vascular disease, a sickle cell disease, an atherosclerosis, a diabetes or an autoimmune disorder.

According to one embodiment, when the progenitor cells are epithelial progenitor cells the disease is a medical condition comprising a ulcer, an inflammatory bowel disease (IBD), a Crohn's disease, an ulcerative colitis, an Alzheimer's disease, a wound healing defect, a cancer, a chronic obstructive pulmonary disease (COPD), a pulmonary fibrosis, an idiopathic pulmonary fibrosis, a pulmonary hypertension, a lung cancer, a sarcoidosis, an acute lung injury (adult respiratory distress syndrome), a respiratory distress syndrome of prematurity, a chronic lung disease of prematurity (bronchopulmonary dysplasia), a surfactant protein B deficiency, a congenital diaphragmatic hernia, a pulmonary alveolar proteinosis, a pulmonary hypoplasia, a lung injury or a corneal degeneration.

According to one embodiment, when the hematopoietic cells which are not stem cells comprise immune cells the disease is a medical condition comprising a malignancy, an autoimmune disease or an infectious disease.

Depending on the application, the method may be effected using cells in suspension (i.e. non-hematopoietic cells or hematopoietic cells which are not stem cells) and/or anti-third party Tcm cells which are syngeneic or non-syngeneic with the subject.

According to one embodiment, the anti-third party cells having the Tcm phenotype are syngeneic with the subject (e.g. autologous).

According to one embodiment, when the anti-third party cells having the Tcm phenotype are syngeneic with the subject (e.g. autologous), the cells in suspension (i.e. non-hematopoietic cells or hematopoietic cells which are not stem cells) are syngeneic or non-syngeneic with the subject.

According to one embodiment, the anti-third party cells having the Tcm phenotype are non-syngeneic with the subject.

According to one embodiment, when the anti-third party cells having the Tcm phenotype are non-syngeneic with the subject (e.g. allogeneic), the cells in suspension (i.e. non-hematopoietic cells or hematopoietic cells which are not stem cells) are syngeneic (e.g. autologous) or non-syngeneic (e.g. allogeneic) with the subject.

According to one embodiment, the cells in suspension (i.e. non-hematopoietic cells or hematopoietic cells which are not stem cells) and the anti-third party cells having the Tcm phenotype are obtained from the same donor (e.g. human being).

According to one embodiment, the cells in suspension (i.e. non-hematopoietic cells or hematopoietic cells which are not stem cells) and the anti-third party cells having the Tcm phenotype are obtained from different donors (e.g. human beings).

According to the method of the present invention, the anti-third party Tcm cells and the cells in suspension (i.e. non-hematopoietic cells or hematopoietic cells which are not stem cells) may be administered concomitantly (e.g. at the same time or on the same day, e.g. within 12-24 hours). Alternatively, the anti-third party Tcm cells may be administered prior to the transplantation of the cells in suspension (i.e. non-hematopoietic cells or hematopoietic cells which are not stem cells). Thus, the anti-third party cells may be administered a day, a week, a month or even several weeks or months prior to administration of the cells. In such a situation it is advisable to monitor the survival of the Tcm cells in the subject (e.g. by FACS or ELISA of a blood test drawn from the subject) prior to administration of the cells in suspension (i.e. non-hematopoietic cells or hematopoietic cells which are not stem cells). According to another embodiment, the anti-third party Tcm cells may be administered following transplantation of the cells in suspension (i.e. non-hematopoietic cells or hematopoietic cells which are not stem cells). Thus, the anti-third party cells may be administered a day, a week, a month or even several weeks or months following administration of the cells in suspension (e.g. in situations where it can facilitate engraftment of the cells or help eliminate graft rejection or GVHD).

According to one embodiment, the anti-third party Tcm cells may be administered to the subject at least twice. According to an embodiment, the Tcm cells may be administered to the subject two, three, four, five times or more. The anti-third party cells may be administered to the subject prior to transplantation of the cells (as discussed above), concomitantly with (as discussed above), or following administration of the differentiated cells (e.g. a day, a week, a month or even several weeks or months following administration of the cells in suspension). Likewise, the cells in suspension (i.e. non-hematopoietic cells or hematopoietic cells which are not stem cells) may be administered in more than one administration (e.g. two, three, four, five or more). Such a determination is well within the capability of one of skill in the art.

The anti-third party Tcm cells and/or the cells in suspension (i.e. non-hematopoietic cells or hematopoietic cells which are not stem cells) of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the anti-third party Tcm cells and/or the cells in suspension (i.e. non-hematopoietic cells or hematopoietic cells which are not stem cells) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Administering the anti-third party Tcm cells and/or the cells in suspension (i.e. non-hematopoietic cells or hematopoietic cells which are not stem cells) into the subject may be effected in numerous ways, depending on various parameters, such as, for example, the cell type; the type, stage or severity of the recipient's disease (e.g. organ failure); the physical or physiological parameters specific to the subject; and/or the desired therapeutic outcome.

For example, depending on the application and purpose, administration of the anti-third party Tcm cells and the cells (in suspension) may be effected by a route selected from the group consisting of intratracheal, intrabronchial, intraalveolar, intravenous, intraperitoneal, intranasal, subcutaneous, intramedullary, intrathecal, intraventricular, intracardiac, intramuscular, intraserosal, intramucosal, transmucosal, transnasal, rectal and intestinal.

According to one embodiment, administering is effected by an intravenous route.

Alternatively, administration to the subject of the anti-third party Tcm cells and/or the cells in suspension (i.e. non-hematopoietic cells or hematopoietic cells which are not stem cells) may be effected by administration thereof into various suitable anatomical locations so as to be of therapeutic effect. Thus, depending on the application and purpose, the cells may be administered into a homotopic anatomical location (a normal anatomical location for the organ or tissue type of the cells), or into an ectopic anatomical location (an abnormal anatomical location for the organ or tissue type of the cells).

Accordingly, depending on the application and purpose, the cells may be advantageously implanted (e.g. transplanted) under the renal capsule, or into the kidney, the testicular fat, the sub cutis, the omentum, the portal vein, the liver, the spleen, the heart cavity, the heart, the chest cavity, the lung, the pancreas, the skin and/or the intra abdominal space.

For example, for the treatment of a liver disease or condition (e.g. liver dysfunction or failure), cells in suspension (i.e. non-hematopoietic cells or hematopoietic cells which are not stem cells) may be transplanted into the liver, the portal vein, the renal capsule, the sub-cutis, the omentum, the spleen, and the intra-abdominal space. Similarly, for the treatment of a pancreatic disease or condition (e.g. diabetes) transplanting cells in suspension (i.e. non-hematopoietic cells or hematopoietic cells which are not stem cells) according to the present invention may be advantageously effected by transplanting the cells into the portal vein, the liver, the pancreas, the testicular fat, the sub-cutis, the omentum, an intestinal loop (the subserosa of a U loop of the small intestine) and/or the intra-abdominal space. For treatment of a pulmonary disease or condition, the cells in suspension may be administered into the lung, under the renal capsule, the liver, the portal vein, the sub-cutis, the omentum, the spleen, the intra-abdominal space, the pancreas and/or the testicular fat. Likewise, transplantation of cells in suspension (i.e. non-hematopoietic cells or hematopoietic cells which are not stem cells) may be carried out for the purpose of treating recipients suffering from, for example, renal failure, heart failure or brain damage.

Optionally, when transplanting the cells of the present invention into a subject having a defective organ, it may be advantageous to first at least partially remove the failed organ from the subject so as to enable optimal development of the transplant, and structural/functional integration thereof with the anatomy/physiology of the subject.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (the anti-third party Tcm cells and/or the cells in suspension (i.e. non-hematopoietic cells or hematopoietic cells which are not stem cells)) effective to prevent, alleviate or ameliorate symptoms of a disorder (e.g., cancer, infectious disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved (as discussed in detail hereinabove).

The amount of a composition to be administered will, of course, be dependent on the subject being treated, the severity of the affliction, the manner of administration, the judgment of the prescribing physician, etc.

Since non-syngeneic (e.g. allogeneic) cells are likely to induce an immune reaction when administered to the subject several approaches have been developed to reduce the likelihood of rejection of non-syngeneic cells. These include either suppressing the recipient immune system or encapsulating the non-autologous cells in immunoisolating, semipermeable membranes before transplantation. Alternatively, cells may be uses which do not express xenogenic surface antigens, such as those developed in transgenic animals (e.g. pigs).

Following transplantation of the cells in suspension (i.e. non-hematopoietic cells or hematopoietic cells which are not stem cells) into the subject according to the present teachings, it is advisable, according to standard medical practice, to monitor the survival and functionality of the cells according to any one of various standard art techniques. For example, the functionality of pancreatic cells may be monitored following transplantation by standard pancreas function tests (e.g. analysis of serum levels of insulin). Likewise, a liver cell transplant may be monitored following transplantation by standard liver function tests (e.g. analysis of serum levels of albumin, total protein, ALT, AST, and bilirubin, and analysis of blood-clotting time). Structural development of the cells may be monitored via computerized tomography, or ultrasound imaging.

Depending on the transplantation context, in order to facilitate engraftment of the cells in suspension (i.e. non-hematopoietic cells or hematopoietic cells which are not stem cells), the method may further advantageously comprise conditioning the subject under sublethal, lethal or supralethal conditions prior to the transplanting.

As used herein, the terms "sublethal", "lethal", and "supralethal", when relating to conditioning of subjects of the present invention, refer to myelotoxic and/or lymphocytotoxic treatments which, when applied to a representative population of the subjects, respectively, are typically: non-lethal to essentially all members of the population; lethal to some but not all members of the population; or lethal to essentially all members of the population under normal conditions of sterility.

According to some embodiments of the invention, the sublethal, lethal or supralethal conditioning comprises a total body irradiation (TBI), total lymphoid irradiation (TLI, i.e. exposure of all lymph nodes, the thymus, and spleen), partial body irradiation (e.g. specific exposure of the lungs, kidney, brain etc.), myeloablative conditioning and/or non-myeloablative conditioning, e.g. with different combinations including, but not limited to, co-stimulatory blockade, chemotherapeutic agent and/or antibody immunotherapy. According to some embodiments of the invention, the conditioning comprises a combination of any of the above described conditioning protocols (e.g. chemotherapeutic agent and TBI, co-stimulatory blockade and chemotherapeutic agent, antibody immunotherapy and chemotherapeutic agent, etc.).

According to one embodiment, the TBI comprises a single or fractionated irradiation dose within the range of 0.5-1 Gy, 0.5-1.5 Gy, 0.5-2.5 Gy, 0.5-5 Gy, 0.5-7.5 Gy, 0.5-10 Gy, 0.5-15 Gy, 1-1.5 Gy, 1-2 Gy, 1-2.5 Gy, 1-3 Gy, 1-3.5 Gy, 1-4 Gy, 1-4.5 Gy, 1-1.5 Gy, 1-7.5 Gy, 1-10 Gy, 2-3 Gy, 2-4 Gy, 2-5 Gy, 2-6 Gy, 2-7 Gy, 2-8 Gy, 2-9 Gy, 2-10 Gy, 3-4 Gy, 3-5 Gy, 3-6 Gy, 3-7 Gy, 3-8 Gy, 3-9 Gy, 3-10 Gy, 4-5 Gy, 4-6 Gy, 4-7 Gy, 4-8 Gy, 4-9 Gy, 4-10 Gy, 5-6 Gy, 5-7 Gy, 5-8 Gy, 5-9 Gy, 5-10 Gy, 6-7 Gy, 6-8 Gy, 6-9 Gy, 6-10 Gy, 7-8 Gy, 7-9 Gy, 7-10 Gy, 8-9 Gy, 8-10 Gy, 10-12 Gy or 10-15 Gy.

According to a specific embodiment, the TBI comprises a single or fractionated irradiation dose within the range of 1-7.5 Gy.

According to one embodiment, the conditioning step is effected by conditioning the subject under supralethal conditions, such as under myeloablative conditions.

Alternatively, the conditioning step may be effected by conditioning the subject under lethal or sublethal conditions, such as by conditioning the subject under myeloreductive conditions or non-myeloablative conditions.

According to one embodiment, the conditioning step is effected by conditioning the subject with a myeloablative drug (e.g. Busulfan or Melfaln) or a non-myeloablative drug (e.g. Cyclophosphamide and or Fludarabin).

Examples of conditioning agents which may be used to condition the subject include, without limitation, irradiation, pharmacological agents, and tolerance-inducing cells (as described herein).

Examples of pharmacological agents include myelotoxic drugs, lymphocytotoxic drugs and immunosuppressant drugs (discussed in detail below).

Examples of myelotoxic drugs include, without limitation, busulfan, dimethyl mileran, melphalan and thiotepa.

Additionally or alternatively, the method may further comprise conditioning the subject with an immunosuppressive regimen prior to, concomitantly with, or following transplantation of the cells in suspension (i.e. non-hematopoietic cells or hematopoietic cells which are not stem cells).

Examples of suitable types of immunosuppressive regimens include administration of immunosuppressive drugs, tolerance inducing cell populations (e.g. anti-third party Tcm cells, as described in detail hereinabove), and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Preferably, the immunosuppressive regimen consists of administering at least one immunosuppressant agent to the subject.

Examples of immunosuppressive agents include, but are not limited to, Tacrolimus (also referred to as FK-506 or fujimycin, trade names: Prograf, Advagraf, Protopic), Mycophenolate Mofetil, Mycophenolate Sodium, Prednisone, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, tramadol, rapamycin (sirolimus) and rapamycin analogs (such as CCI-779, RAD001, AP23573). These agents may be administered individually or in combination.

The therapeutic compositions of the present invention may, if desired, be presented in a pack or dispenser device, such as an FDA approved kit, which may contain one or more unit dosage forms containing the active ingredients.

Thus, according to one aspect of the invention, there is provided a kit for transplantation comprising: (i) cells in suspension wherein the cells comprise non-hematopoietic cells or hematopoietic cells which are not stem cells; and (ii) anti-third party cells having a central memory T-lymphocyte (Tcm) phenotype, the cells being tolerance-inducing cells and capable of homing to the lymph nodes following transplantation.

The cells in the kit may be formulated for intravenous administration.

According to one embodiment, the cells in suspension (i.e. non-hematopoietic cells or hematopoietic cells which are not stem cells) and the anti-third party cells having the Tcm phenotype are comprised in a single container. According to another embodiment, the cells in suspension (i.e. non-hematopoietic cells or hematopoietic cells which are not stem cells) and the anti-third party cells having the Tcm phenotype are comprised in separate containers.

The kit may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to one embodiment, the kit further comprises a chemotherapeutic agent (e.g. antineoplastic agent). According to a specific embodiment, the chemotherapeutic agent comprises an Alkylating agent. Exemplary Alkylating agents include, but are not limited to, Cyclophosphamide, Busulfan, Mechlorethamine or mustine (HN2), Uramustine or uracil mustard, Melphalan, Chlorambucil, Ifosfamide, Bendamustine, Nitrosoureas Carmustine, Lomustine, Streptozocin, Thiotepa, Platinum, Cisplatin, Carboplatin, Nedaplatin, Oxaliplatin, Satraplatin, Triplatin tetranitrate, Procarbazine, Altretamine, Triazenes (dacarbazine, mitozolomide, temozolomide), Dacarbazine, Temozolomide, Myleran, Busulfex, Fludarabine and Dimethyl mileran.

According to one embodiment, the kit further comprises an anti-rejection agent (e.g. an immunosuppressant). Exemplary immunosuppressants are described in detail hereinabove.

According to one embodiment, the kit further comprises an antiviral agent.

According to a specific embodiment, the antiviral agent comprises a Ganciclovir, a Valaciclovir, an Acyclovir, a Valganciclovir, a Foscarnet, a Cidofovir, a Maribavir, or a Leflunomide.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND EXPERIMENTAL PROCEDURES

Animals

Female 6 to 12 week old BALB/c, CB6 (F1) and C57BL/6 mice were obtained from Harlan Laboratories or grown at the animal facility at Weizmann Institute of Science. All mice were kept in small cages (5 animals in each cage) and fed sterile food and acid water. All studies were approved by the Weizmann Institute of Science Institutional Animal Care and Use Committee.

Preparation of Host Nonreactive Mouse Anti-3$^{rd}$-Party Tcm

Anti-third-party Tcm were prepared as previously described [Ophir E et al., Blood (2010) 115: 2095-2104] briefly, splenocytes of the donor mice were cultured against irradiated third-party splenocytes for 60 hours under cytokine deprivation. Subsequently, CD8$^+$ cells were positively selected using Magnetic Particles (BD Pharmingen) and cultured in an Ag-free environment. rhIL-15 (20 ng/mL; R&D Systems) was added every second day. To attain a purified population at the end of the culture (day 16), the Tcm cells were positively selected for CD62L expression by magnetic-activated cell sorting [MACS, Miltenyi, Bergisch Gladbach, Germany].

Bone Marrow Transplant

1. Long bones were harvested from Balb/c or C57BL/6 mice [either Nude or wild type (WT)]. Bone marrow was extracted by flushing or grinding the bones to reach a single cell suspension. Some preparations harvested from WT mice were subjected to T-cell depletion by magnetic-activated cell sorting. Bone marrow was counted and brought to the correct concentration and was then injected to mice i.v. to the tail vein or intra-orbitally.

2. Prior to transplantation, the mice were subjected to a conditioning regimen. Reduced intensity conditioning (RIC) comprised either subjecting the mice to sub-lethal irradiation doses (i.e. irradiation dose which recipient mice could recover from spontaneously) or subjecting the mice to low dosage of myeloablative (e.g. Busulfan) or non-myeloablative (e.g. Cyclophosphamide) drugs. Total body irradiation (TBI) was administered using either gamma-ray machine or x-ray (e.g. XRAD-320). Drugs were administered by i.v., s.c., i.p. or orally.

OT1+ Cell Transplantation

Lymph nodes and/or spleens were harvested from OT-1 transgenic mice. Mice were either OT-1 mice carrying CD45.1 gene and/or on the background of a RAG−/− mutation. Alternatively, OT-1 mice were F1-OT1 mice, progeny of hostXOT-1 mice, useful for elimination of allogeneic phenomena. Single cell suspensions were created and were then subjected to T-cell purification by magnetic-activated cell sorting [MACS, Miltenyi, Bergisch Gladbach, Germany]. Purity of the resulting OT-1 T-cell population was tested via FACS. Cells were then injected as 'fresh' cells or otherwise were cultured ex-vivo to produce Tcm cells as described above, i.e. by third party activation towards irradiated splenocytes from an ovalbumin expressing mouse. OT-1 Tcm cells were then injected as described herein.

Flow Cytometric Analysis

Fluorescence-activated cell sorting (FACS) analysis was performed using a modified Becton Dickinson FACScan. Cells were stained with labeled antibodies specific for Vα2, Vβ5, H2Dd, H2Kb, CD45.1, CD45.2, CD8a, CD4, CD25, CD69, CD19 (Biolegend; BD; Miltenyi).

CTL Activity Assay ($^{51}$Cr Assay)

Mice were sacrificed, spleens and LNs were harvested and cells were selected for CD8$^+$ (and negatively selected for H-2D$^d$ to exclude 'Tcm'). These naive HTC were tested for their killing ability of either C3H (H-2$^k$) or BALB/c (H-2$^d$) targets in a chromium release assay. BALB/c and C3H splenocytes, used as target cells, were pretreated with 2 µg/ml concanavalin A (Sigma, St. Louis, Mo.) for 48 hours and exposed to 70 µCi $^{51}$Cr (Perkin Elmer, Wellesley, Mass.) for 1 hour. Effector cells were prepared from CD8+ selected cells from C57BL/6 mice and were incubated for 6 days in different dilutions against BALB/c or C3H splenocytes in 12 replicates for each dilution in a 96-well plate with IL-2 (20 U/ml). At day 6, titrated numbers of effector cells and 5×10$^3$ $^{51}$Cr-labeled targets were mixed in V-shape bottomed plates at various effector/target (E:T) ratios. Cytotoxic activity was measured in a 4 hour $^{51}$Cr release assay. Percentage of specific lysis was calculated as (experimental release− spontaneous release)/(maximal release−spontaneous release)×100. The release of $^{51}$Cr by target cells cultured in medium alone, or lysed with 1% SDS, was defined as spontaneous release or total release, respectively.

Peripheral Blood Mononuclear Cells (PBMCs)

PBMCs were isolated from whole blood of patients and from healthy volunteers by Ficoll density gradient centrifugation. When indicated the cells were typed for Class I HLA by serological methods as previously described [Manual of Tissue Typing Techniques. Washington D.C., National Institute of Allergy and Infectious Diseases, NIH DHEW Publication 76-545, 1976, p 22].

Dendritic Cell Generation

Monocytes were isolated by plastic adherence and cultured in 6-well plates using 3 ml of Cellgro DC medium supplemented with 1% human serum and penicillin/streptomycin plus GM-CSF (800 IU/ml) and IL-4 (20 ng/ml) (Peprotech, Hamburg, Germany). After 48 h of culture, 1.5 ml of medium was added (+GM-CSF at 1600 IU/ml and IL4 at 20 ng/ml). 24 h later, non-adherent cells were harvested, and large cells (mostly immature DC) were counted, resuspended in fresh medium containing GM-CSF 800 IU/ml, IL-4 20 ng/ml, LPS from *E. coli* 055:B5 at 10 ng/ml (Sigma, Deisenhofen, Germany) and IFNγ (Peprotech, 100 IU/ml), and plated at approximately 106 DC per well in 2 ml and incubated overnight. The next day, non-adherent cells were discarded, and adherent DC were gently removed using cold PBS/1% HS after incubation on ice for 20 minutes. Large cells consisting of mature DC were counted. The cells were irradiated with 30 Gy to avoid outgrowth of few potentially contaminating NK- or memory T-cells and were then used for T-cell stimulation.

Isolation of Naïve CD8 T-Cells from PBMCs

Naïve CD8 T cells were isolated by initial negative selection using a CD8 negative selection kit (Miltenyi, Bergisch Gladbach, Germany) according to the manufacturer's instructions. Antigen-experienced CD8+ T-cells were then depleted using CD45RO− beads and on LD column.

Generation of Anti-3rd Party Central Memory Human CD8 T-Cells

Naïve CD8 T cells were isolated and resuspended in T-cell medium supplemented with IL-21 (Peprotech, 30 ng/ml). Irradiated DCs were added at a 1:4 DC:T-cell ratio with 4×10$^5$ T-cells per well of a 48-well plate. Total volume of each well was 500 µl. 72 h after initiation of the culture, 500 µl T-cell medium with IL-7 and IL-15 (Peprotech, 5 ng/ml final concentrations) were added and cells were subsequently fed every 2-3 days as outline in the results section.

Statistical Analysis

The analysis of survival data was performed using Kaplan-Meier curves (log-rank test). Comparison of means was conducted using the Student t test.

Example 1

Figure 1B:
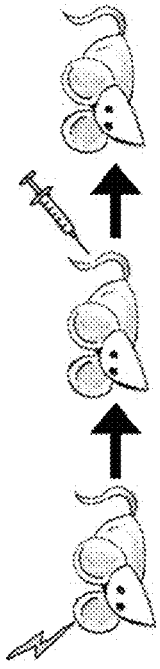

MHC Mismatched Tcm Survive in Host Mice Under Syngeneic Bone Marrow Settings and Exert Specific Veto Activity Considering that syngeneic bone marrow transplant (BMT), even when administered in the context of lethal total body irradiation (TBI) is by far safer in humans compared to allogeneic BMT, the present inventors first sought out to determine whether adoptively transferred F1-Tcm cells survive the attack of host anti-donor HTC when infused in conjunction with syngeneic TDBMT (FIGS. 1A-B). As can be seen in FIGS. 2A-B, F1-Tcm persisted in the peripheral blood at day 60 post-transplantation. Tcm cells comprised some 13%±10 of the total CD8$^+$ compartment (data not shown). Next, to evaluate the ability of Tcm to induce deletion of antigen-specific clones within the wild type polyclonal HTC population and to verify that remaining HTCs retain their functionality, a chromium release killing assay was employed. Results show that H2$^b$CD8$^+$HTC from Tcm treated mice displayed significantly reduced killing of H-2$^d$ targets and retained killing capacity of H-2$^k$ targets, while mice not treated with Tcm (i.e. BM alone group) displayed similar levels of killing for both cell types (FIG. 3). These results indicate that Tcm exert specific-veto activity upon a polyclonal-HTC population and confirm that the clones not deleted by the Tcm, retain their functionality. Subsequently, these experiments were repeated in mice conditioned with reduced intensity conditioning (RIC), more suitable for clinical implementation. Hence, studies in 5.5 Gy TBI sublethally irradiated Balb/c mice, injected with syngeneic T cell depleted bone marrow (TDBMT) and allogeneic (Balb×Black) F1 Tcm (illustrated in FIG. 1C), yielded similar results (FIG. 4). Tcm cells were present in peripheral blood of these mice for more than 15 months (when experiment was terminated, data not shown). Thus, the survival of MHC mismatched Tcm can be induced under a very safe procedure involving conditioning with sub-lethal 5.5 Gy TBI and autologous BMT.

Example 2

Figure 1C:
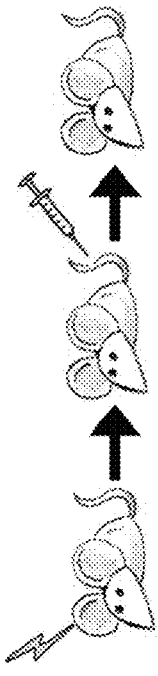

MHC Mismatched Tcm Survive in Host Mice in the Absence of a Bone Marrow Transplant In light of the above data, the ability of the Tcm cells alone to induce tolerance in the absence of BM was assessed. The outreach of such a protocol would be far greater. Specifically, induction of immune tolerance through administration of anti-3$^{rd}$-party Tcm cells alone, under safe conditioning, would be an asset not only for immune compromised individuals, but could possibly allow for the treatment of non-malignant hematological diseases (e.g. anemia & thalassemia), autoimmune diseases and could provide a platform for cell therapy administration. Initially the present inventors attempted to define the minimal irradiation dose under which Tcm cells of F1 origin engraft, in order to set up the model in which tolerance induction in hosts can be tested. To this end, Balb/c mice were exposed to a range of sublethal conditioning doses with and without adoptive transfer of CB6 F1-Tcm cells. Analysis of whole peripheral blood for H2$^{db}$-positive Tcm cells showed that the minimal irradiation dose under which Tcm could be detected (i.e. where Tcm cells were not rejected) was 5.5 Gy TBI (FIG. 5). Consequently, sustainability of fully allogeneic C57BL/6 derived Tcm to survive under a sublethal TBI dose of 5.5 Gy was tested (as depicted in FIG. 1C). This experiment was intended to verify that cells of allogeneic origin do not induce GVHD and that the deletion of anti-donor T cells is not mediated through alloreactivity but rather by veto activity. Moreover, once translated to humans and in order to produce "off-the-shelf" tolerance inducing Tcm, cells will most probably be derived from allogeneic, non-matched, sources. Results showed that C57BL/6 derived allogeneic Tcm were able to survive within 5.5 Gy irradiated Balb/c hosts (as depicted in FIG. 1C), displaying slightly lower Tcm percentages in the peripheral blood than those in mice receiving CB6 F1 Tcm (FIGS. 6A-B). This result may be attributed to a very slow rejection process of the Tcm cells. Although Tcm cells persist in the blood for well over a year, the reduction in their number over the first few months post injection, taken together with the elimination of anti-host clones detected in the chromium release assay, strongly suggests that the Tcm induce peripheral tolerance.

Therefore the application of Tcm-alone could be used to create a window of opportunity, at least for few months, for administration of treatments, such as cell-therapy.

Example 3

MHC Mismatched Tcm Support Adoptive Transfer of Cells from the Same Donor

To test the hypothesis that Tcm cells can be used for adoptive cell therapy, the present inventors utilized a transgenic OT1 mice that carries a TCR against the ovalbumin peptide. The motivation to use OT1 transgenic cells in this context stemmed from the idea that these cells can be used as a model for cell-therapies known as donor lymphocyte infusion (DLI) with the whole population of donor T cells or with antigen specific T cells directed against viral or tumor antigens.

Initially, naïve CD8$^+$OT1$^+$CD45.1$^+$ T cells were infused into the Tcm chimeric mice, 90 days post initial adoptive transfer of the Tcm. The main goal was to define whether the surviving Tcm population can facilitate engraftment of newly infused allogeneic cells. Prior to injection of naïve Tg cells the Tcm population in chimeric mice were analyzed by FACS. Thus, 2/5 and 9/11 mice that had received C57BL/6 Tcm or CB6-Tcm, respectively, maintained their Tcm population (FIGS. 6A-B).

These mice were further conditioned on day 90 post-transplantation with 2 Gy TBI (in order to deplete some T cells to allow for the new T cells to be introduced) and the mice were then infused with 2×10$^6$ OT1 cells (H-2$^b$). Interestingly, when evaluated on day 120 (30 days post OT1 cell transplantation) the OT1 cells could be detected only in those mice that had displayed a Tcm population prior to transplantation (FIG. 7). These preliminary results, showing that in mice displaying a population of Tcm addition of cells from the same donor origin can be accepted, were further substantiated using transgenic OT-1 cells, as follows: CD8+ OT-1 cells were transplanted along with the Tcm on day 0, to prevent the need for secondary conditioning (2 Gy TBI previously employed on day 90), and the presence of OT1 cells in the peripheral blood was monitored at different time points after cell infusion.

As shown in FIG. 8, the results of this experiment illustrate that:

1. C57BL/6 Tcm as well as (BalbxC57BL)F1 Tcm can persist in allogeneic recipients.
2. C57BL/6 Tcm can confer protection to CD8+OT-1 naïve cells bred on C57BL/6 background (OT-1+CD45.1+ RAG−) when co-injected, while OT-1 cells on their own fade away from circulation.
3. CB6(F1) Tcm that express the MHC haplotype of C57BL/6 (H-2$^b$) mice can also confer protection of OT-1 naïve cells.

Example 4

MHC Mismatched Tcm Support Adoptive Transfer of CAR T Cells from the Same Donor

Patients with Acute lymphocytic leukemia (ALL) are conditioned with sublethal conditioning protocol (5.0 Gy TBI) one day prior to transplantation (on day −1). The next day (Day 0), the patient is transplanted (by infusion) with 1×10$^7$/Kg Tcm cells (generated as discussed above) along with 1×10$^7$/Kg CAR T cells directed against CD19.

Example 5

Anti-Third Party Tcm Cells can Support Engraftment of Anti-Tumor TCR Transgenic Donor-Derived CD8+ Cells Enabling Eradication of Melanoma Tumor Cells As illustrated in FIG. 9, the present inventors have utilized a B16-melanoma residual disease prevention model in which B16-OVA expressing melanoma cells (H2$^b$) were injected (on day −2) into C57BL/6 mice (H2$^b$). The following day (day −1), these mice were treated by RIC with TBI. The following day, tumor bearing C57BL/6 mice were administered anti-Ova TCR transgenic OT1-F1 (H2$^{db}$) fresh cells alone or concomitantly with F1 Tcm cells (i.e. from the same cell donor) or with allogeneic Balb/c Tcm cells bearing the non-shared MHC (H2$^d$). As illustrated in FIG. 10, fresh OT1 cells from (Black×Balb) F1 origin failed to inhibit growth of host type melanoma tumor expressing the OVA antigen (see FIG. 10, red column). Of note, mice bearing the tumor are C57BL/6 and they are capable of rejecting the F1 OT1 cells as these cells express the MHC of Balb. However, when Tcm veto cells expressing MHC of Balb origin (i.e. Tcm cells of the same F1 donor or Tcm cells of an allogeneic Balb/c background) were administered, they supported the engraftment and survival of the fresh OT1 cells by virtue of veto mechanism and significantly enhanced the anti-tumor activity of the OT1 cells. Accordingly, in mice receiving Tcm cells tumor size was reduced by more than 3.5 fold).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of transplantation of cells in suspension, the method comprising:
   (a) administering to a subject in need of transplantation of cells in suspension, a therapeutically effective amount of anti-third party cells having a central memory T-lymphocyte (Tcm) phenotype, said anti-third party cells being tolerance-inducing cells and capable of homing to the lymph nodes following transplantation; and
   (b) administering said cells in suspension to the subject, wherein said cells in suspension comprise:
   mesenchymal stem cells, endothelial progenitor cells and/or epithelial progenitor cells; or
   hematopoietic cells which are not stem cells.

2. The method of claim 1, wherein said mesenchymal stem cells, endothelial progenitor cells and/or epithelial progenitor cells are obtained from a fetal tissue.

3. The method of claim 1, wherein said mesenchymal stem cells, endothelial progenitor cells and/or epithelial progenitor cells are obtained from an adult tissue.

4. The method of claim 1, wherein said hematopoietic cells which are not stem cells comprise a subpopulation of lymphatic cells or immune cells.

5. The method of claim 4, wherein said immune cells are selected from the group consisting of T cells, B cells, NK cells, NKT cells and dendritic cells (DCs).

6. The method of claim 5, wherein said T cells are selected from the group consisting of CD4+ T cells, CD8+ T cells, tumor infiltrating lymphocytes (TIL) and tumor-associated lymphocytes (TALs).

7. The method of claim 1, wherein said hematopoietic cells which are not stem cells are genetically modified.

8. The method of claim 7, wherein said genetically modified cells comprise genetically modified immune cells.

9. The method of claim 8, wherein said immune cells express a chimeric antigen receptor (CAR) or a modified T cell receptor (TCR).

10. The method of claim 9, wherein said immune cells are T cells.

11. The method of claim 1, wherein said administering to said subject a therapeutically effective amount of said anti-third party cells having said Tem phenotype is effected at least twice.

12. The method of claim 1, wherein said subject in need of transplantation has a malignant disease.

13. The method of claim 12, wherein said malignant disease is a solid tumor or tumor metastasis.

14. The method of claim 12, wherein said malignant disease is a hematological malignancy.

15. The method of claim 12, wherein said malignant disease is selected from the group consisting of a lung cancer, a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer and a pancreatic cancer.

16. The method of claim 1, wherein said subject in need of transplantation has a non-malignant disease.

17. The method of claim 16, wherein said non-malignant disease is selected from the group consisting of an organ dysfunction or failure, an infectious disease, an autoimmune disease and an injury.

18. The method of claim 16, wherein said non-malignant disease is selected from the group consisting of a Parkinson's disease, an Alzheimer's disease, a multiple sclerosis, a retinal disease, a diabetes mellitus, a cerebral ischemia, a myogenic disease, a pulmonary disease, a renal disease, a hepatic disease, a cardiac disease, a gastrointestinal tract disease, a skin disease, a fertility disease and a brain disease.

19. The method of claim 16, wherein when:
the cells are mesenchymal stem cells the disease is a medical condition selected from the group consisting of a cosmetic condition, a tissue or organ damage, an orthopedic condition, a neural condition, a heart disease or condition, a diabetes, a deafness, a Crohn's disease, an autoimmune disorder, a leukemia, a cancer, a sickle cell disease, an amyotrophic lateral sclerosis and a metabolic disorders; or
the cells are endothelial cells the disease is a medical condition selected from the group consisting of a bone disease, a bone damage, a cardiovascular disease, a cardiovascular injury, an ischemic disease, an ischemic injury, a vascular disease, a sickle cell disease, an atherosclerosis, a diabetes and an autoimmune disorder; or
the cells are epithelial cells the disease is a medical condition selected from the group consisting of a ulcer, an inflammatory bowel disease (IBD), a Crohn's disease, an ulcerative colitis, an Alzheimer's disease, a wound healing defect, a cancer, a chronic obstructive pulmonary disease (COPD), a pulmonary fibrosis, an idiopatic pulmonary fibrosis, a pulmonary hypertension, a lung cancer, a sarcoidosis, an acute lung injury (adult respiratory distress syndrome), a respiratory distress syndrome of prematurity, a chronic lung disease of prematurity (bronchopulmonary dysplasia), a surfactant protein B deficiency, a congenital diaphragmatic hernia, a pulmonary alveolar proteinosis, a pulmonary hypoplasia, a lung injury and a corneal degeneration.

20. The method of claim 4, wherein when the hematopoietic cells which are not stem cells comprise immune cells the disease is a medical condition selected from the group consisting of a malignancy, an autoimmunc disease and an infectious disease.

21. The method of claim 1, wherein said hematopoietic cells which are not stem cells and said anti-third party cells having said Tcm phenotype are obtained from the same donor.

22. The method of claim 1, wherein said anti-third party cells having said Tcm phenotype comprise a $CD3^+$, $CD8^+$, $CD62L^+$, $CD45RA^-$, $CD45RO^+$ signature.

23. The method of claim 22, wherein at least 50% of the isolated population of cells are CD3+CD8+ cells of which at least 50% have said signature.

24. The method of claim 1, further comprising conditioning the subject under sublethal, lethal or supralethal conditioning protocol prior to said administering.

25. The method of claim 1, wherein said subject is a human subject.

26. The method of claim 1, wherein said anti-third party cells having said Tcm phenotype are generated by a method comprising:
(a) contacting peripheral blood mononuclear cells (PBMCs) with a third party antigen or antigens in the presence of IL-21 so as to allow enrichment of antigen reactive cells; and
(b) culturing said cells resulting from step (a) in the presence of IL-21, IL-15 and IL-7 so as to allow proliferation of cells comprising said central memory T-lymphocyte (Tcm) anti-third party phenotype, thereby generating the anti-third party cells having said Tcm phenotype.

27. The method of claim 26, further comprising depleting adherent cells from said PBMCs prior to said contacting with said third party antigen or antigens.

28. The method, of claim 26, further comprising depleting CD4+ and/or CD56+ cells from said PBMCs prior to said contacting with said third party antigen or antigens.

29. The method of claim 26, further comprising selecting for activated cells following step (a) and prior to step (b).

30. The method of claim 1, wherein step (a) and step (b) are carried out concomitantly.

31. The method of claim 1, wherein step (h) is carried out prior to step (a).

* * * * *